US005801045A

United States Patent [19]

Weber et al.

[11] Patent Number: 5,801,045
[45] Date of Patent: Sep. 1, 1998

[54] COLLAGEN-LIKE POLYPEPTIDES AND BIOPOLYMERS AND NUCLEIC ACIDS ENCODING SAME

[75] Inventors: Shane Crawford Weber, Woodbridge, Conn.; John Alan McElver, Des Moines, Iowa

[73] Assignee: Eastman Kodak Company, Rochester, N.Y.

[21] Appl. No.: 814,309

[22] Filed: Mar. 10, 1997

Related U.S. Application Data

[62] Division of Ser. No. 383,804, Feb. 3, 1995, Pat. No. 5,670,616.

[51] Int. Cl.$^6$ .................... C12N 1/11; C12N 1/15; C12N 1/21
[52] U.S. Cl. ............ 435/252.3; 435/69.1; 435/320.1; 530/356; 536/23.1; 536/23.5
[58] Field of Search .................... 435/252.3, 69.1, 435/320.1; 530/356; 536/23.1, 23.5

[56] References Cited

U.S. PATENT DOCUMENTS

| 5,089,406 | 2/1992 | Williams et al. ............ 435/172.3 |
| 5,114,840 | 5/1992 | Tryggvason et al. ............ 435/6 |
| 5,149,657 | 9/1992 | Maugh et al. ............ 435/320.1 |
| 5,243,038 | 9/1993 | Ferrari et al. ............ 536/23.1 |
| 5,496,712 | 3/1996 | Cappello et al. ............ 435/69.1 |
| 5,580,712 | 12/1996 | Keevert, Jr. et al. ............ 430/569 |
| 5,670,616 | 9/1997 | Weber et al. ............ 530/300 |

FOREIGN PATENT DOCUMENTS

| 2685347 | 6/1993 | France . |
| 03533 | 5/1988 | WIPO . |
| 05177 | 5/1990 | WIPO . |
| 09695 | 6/1992 | WIPO . |
| 10567 | 6/1992 | WIPO . |

OTHER PUBLICATIONS

Tirrell et al, *MRS Bulletin I*, XVI (7), pp. 22–28, 1991.
Bella et al, *Science*, 266, pp. 75–81, 1994.
Goldberg et al, *Gene*, 80, pp. 305–314, 1989.
Futuretech® Briefing No. 78, Mar. 27, 1989.

*Primary Examiner*—Eric Grimes
*Assistant Examiner*—Enrique D. Longton
*Attorney, Agent, or Firm*—J. Lanny Tucker

[57] ABSTRACT

Synthetic biopolymers can be prepared using recombinant DNA technology or chemical synthetic methods which have properties similar to naturally occuring gelatin or collagen. These materials comprises one or more polypeptides having the peptide sequence represented by the formulae:

I:
$\{[(Gly\ Pro\ Gln)(Gly\ Pro\ Glu)_4]_2\}_n$

II:
$Gly\ Pro\ Glu\{[(Gly\ Pro\ Gln)(Gly\ Pro\ Glu)_4]_2\}_n$

III:
Gly Pro Xaa$_1$ Gly Leu Xaa$_2$ Gly Pro Arg Gly Pro Pro
Gly Ala Ser Gly Ala Pro Gly Pro Glu Gly Phe Gln Gly wherein
Xaa$_1$ and Xaa$_2$ are independently the amino acids identified as Met, Ile, His, Lys, Asn, Tyr or Gln, and n is 1 to 25.

12 Claims, 5 Drawing Sheets

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
        ( A ) LENGTH: 93
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces cerevisiae ( v i i ) IMMEDIATE SOURCE: Saccharomyces cerevisiae ( x ) PUBLICATION INFORMATION: None ( x i ) SEQUENCE DESCRIPTION: SEQ ID NO:1:

```
Gly Pro Glu Gly Pro Gln Gly Pro Glu Gly Pro Glu
                 5                  10
Gly Pro Glu Gly Pro Glu Gly Pro Gln Gly Pro Glu
             15                 20
Gly Pro Glu Gly Pro Glu Gly Pro Glu Gly Pro Gln
 25                  30                  35
Gly Pro Glu Gly Pro Glu Gly Pro Glu Gly Pro Glu
```

```
                        40                          45
Gly Pro Gln Gly Pro Glu Gly Pro Glu Gly Pro Glu
         50                  55                 60
Gly Pro Glu Gly Pro Gln Gly Pro Glu Gly Pro Glu
                 65                  70
Gly Pro Glu Gly Pro Glu Gly Pro Gln Gly Pro Glu
         75                  80
Gly Pro Glu Gly Pro Glu Gly Pro Glu
 85                  90
```

( 2 ) INFORMATION FOR SEQ ID NO:2:

( i ) SEQUENCE CHARACTERISTICS:
        ( A ) LENGTH: 123
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces cerevisiae ( v i i ) IMMEDIATE SOURCE: Saccharomyces cerevisiae ( x ) PUBLICATION INFORMATION: None ( x i ) SEQUENCE DESCRIPTION: SEQ ID NO:2:

```
Gly Pro Glu Gly Pro Gln Gly Pro Glu Gly Pro Glu
                 5                   10
Gly Pro Glu Gly Pro Glu Gly Pro Gln Gly Pro Glu
         15                  20
Gly Pro Glu Gly Pro Glu Gly Pro Glu Gly Pro Gln
 25                  30                  35
Gly Pro Glu Gly Pro Glu Gly Pro Glu Gly Pro Glu
                 40                  45
Gly Pro Gln Gly Pro Glu Gly Pro Glu Gly Pro Glu
         50                  55                 60
Gly Pro Glu Gly Pro Gln Gly Pro Glu Gly Pro Glu
                 65                  70
Gly Pro Glu Gly Pro Glu Gly Pro Gln Gly Pro Glu
         75                  80
Gly Pro Glu Gly Pro Glu Gly Pro Glu Gly Pro Gln
 85                  90                  95
Gly Pro Glu Gly Pro Glu Gly Pro Glu Gly Pro Glu
                 100                 105
Gly Pro Gln Gly Pro Glu Gly Pro Glu Gly Pro Glu
         110                 115                120
Gly Pro Glu
```

( 2 ) INFORMATION FOR SEQ ID NO:3:

( i ) SEQUENCE CHARACTERISTICS:
        ( A ) LENGTH: 273
        ( B ) TYPE: Amino acid
        ( D ) TOPOLOGY: Linear ( i i ) MOLECULE TYPE: Polypeptide (  i i i  ) HYPOTHETICAL: No (  i v  ) ANTI-SENSE: No (  v  ) FRAGMENT TYPE: C-terminal (  v i  ) ORIGINAL SOURCE: Saccharomyces cerevisiae (  v i i  ) IMMEDIATE SOURCE: Saccharomyces cerevisiae (  x  ) PUBLICATION INFORMATION: None (  x i  ) SEQUENCE DESCRIPTION: SEQ ID NO:3:

```
Gly Pro Glu Gly Pro Gln Gly Pro Glu Gly Pro Glu
                  5                  10
Gly Pro Glu Gly Pro Glu Gly Pro Gln Gly Pro Glu
             15                  20
Gly Pro Glu Gly Pro Glu Gly Pro Glu Gly Pro Gln
 25                  30                  35
Gly Pro Glu Gly Pro Glu Gly Pro Glu Gly Pro Glu
             40                  45
Gly Pro Gln Gly Pro Glu Gly Pro Glu Gly Pro Glu
 50                  55                  60
Gly Pro Glu Gly Pro Gln Gly Pro Glu Gly Pro Glu
             65                  70
Gly Pro Glu Gly Pro Glu Gly Pro Gln Gly Pro Glu
             75                  80
Gly Pro Glu Gly Pro Glu Gly Pro Glu Gly Pro Gln
 85                  90                  95
Gly Pro Glu Gly Pro Glu Gly Pro Glu Gly Pro Glu
            100                 105
Gly Pro Gln Gly Pro Glu Gly Pro Glu Gly Pro Glu
110                 115                 120
Gly Pro Glu Gly Pro Gln Gly Pro Glu Gly Pro Glu
            125                 130
Gly Pro Glu Gly Pro Glu Gly Pro Gln Gly Pro Glu
            135                 140
Gly Pro Glu Gly Pro Glu Gly Pro Glu Gly Pro Gln
145                 150                 155
Gly Pro Glu Gly Pro Glu Gly Pro Glu Gly Pro Glu
            160                 165
Gly Pro Gln Gly Pro Glu Gly Pro Glu Gly Pro Glu
170                 175                 180
Gly Pro Glu Gly Pro Gln Gly Pro Glu Gly Pro Glu
            185                 190
Gly Pro Glu Gly Pro Glu Gly Pro Gln Gly Pro Glu
            195                 200
Gly Pro Glu Gly Pro Glu Gly Pro Glu Gly Pro Gln
205                 210                 215
Gly Pro Glu Gly Pro Glu Gly Pro Glu Gly Pro Glu
            220                 225
Gly Pro Gln Gly Pro Glu Gly Pro Glu Gly Pro Glu
230                 235                 240
Gly Pro Glu Gly Pro Gln Gly Pro Glu Gly Pro Glu
            245                 250
Gly Pro Glu Gly Pro Glu Gly Pro Gln Gly Pro Glu
            255                 260
```

```
Gly Pro Glu Gly Pro Glu Gly Pro Glu
265                 270
```

( 2 ) INFORMATION FOR SEQ ID NO:4:

( i ) SEQUENCE CHARACTERISTICS:
        ( A ) LENGTH: 30
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:4:

```
Gly Pro Gln Gly Pro Glu Gly Pro Glu Gly Pro Glu
              5                   10
Gly Pro Glu Gly Pro Gln Gly Pro Glu Gly Pro Glu
            15                  20
Gly Pro Glu Gly Pro Glu
25              30
```

( 2 ) INFORMATION FOR SEQ ID NO:5:

( i ) SEQUENCE CHARACTERISTICS:
        ( A ) LENGTH: 540
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces cerevisiae ( v i i ) IMMEDIATE SOURCE: Saccharomyces cerevisiae ( x ) PUBLICATION INFORMATION: None ( x i ) SEQUENCE DESCRIPTION: SEQ ID NO:5:

```
Gly Pro Gln Gly Pro Glu Gly Pro Glu Gly Pro Glu
              5                   10
Gly Pro Glu Gly Pro Gln Gly Pro Glu Gly Pro Glu
            15                  20
Gly Pro Glu Gly Pro Glu Gly Pro Gln Gly Pro Glu
        25              30              35
Gly Pro Glu Gly Pro Glu Gly Pro Glu Gly Pro Gln
            40                  45
Gly Pro Glu Gly Pro Glu Gly Pro Glu Gly Pro Glu
        50              55                    60
Gly Pro Gln Gly Pro Glu Gly Pro Glu Gly Pro Glu
                65              70
Gly Pro Glu Gly Pro Gln Gly Pro Glu Gly Pro Glu
            75              80
```

```
Gly Pro Glu Gly Pro Glu Gly Pro Gln Gly Pro Glu
 85              90              95
Gly Pro Glu Gly Pro Glu Gly Pro Glu Gly Pro Gln
            100             105
Gly Pro Glu Gly Pro Glu Gly Pro Glu Gly Pro Glu
            110             115             120
Gly Pro Gln Gly Pro Glu Gly Pro Glu Gly Pro Glu
            125             130
Gly Pro Glu Gly Pro Gln Gly Pro Glu Gly Pro Glu
            135             140
Gly Pro Glu Gly Pro Glu Gly Pro Gln Gly Pro Glu
145             150             155
Gly Pro Glu Gly Pro Glu Gly Pro Glu Gly Pro Gln
            160             165
Gly Pro Glu Gly Pro Glu Gly Pro Glu Gly Pro Glu
            170             175             180
Gly Pro Gln Gly Pro Glu Gly Pro Glu Gly Pro Glu
            185             190
Gly Pro Glu Gly Pro Gln Gly Pro Glu Gly Pro Glu
            195             200
Gly Pro Glu Gly Pro Glu Gly Pro Gln Gly Pro Glu
205             210             215
Gly Pro Glu Gly Pro Glu Gly Pro Glu Gly Pro Gln
            220             225
Gly Pro Glu Gly Pro Glu Gly Pro Glu Gly Pro Glu
            230             235             240
Gly Pro Gln Gly Pro Glu Gly Pro Glu Gly Pro Glu
            245             250
Gly Pro Glu Gly Pro Gln Gly Pro Glu Gly Pro Glu
            255             260
Gly Pro Glu Gly Pro Glu Gly Pro Gln Gly Pro Glu
265             270             275
Gly Pro Glu Gly Pro Glu Gly Pro Glu Gly Pro Gln
            280             285
Gly Pro Glu Gly Pro Glu Gly Pro Glu Gly Pro Glu
290             295             300
Gly Pro Gln Gly Pro Glu Gly Pro Glu Gly Pro Glu
            305             310
Gly Pro Glu Gly Pro Gln Gly Pro Glu Gly Pro Glu
            315             320
Gly Pro Glu Gly Pro Glu Gly Pro Gln Gly Pro Glu
325             330             335
Gly Pro Glu Gly Pro Glu Gly Pro Glu Gly Pro Gln
            340             345
Gly Pro Glu Gly Pro Glu Gly Pro Glu Gly Pro Glu
            350             355             360
Gly Pro Gln Gly Pro Glu Gly Pro Glu Gly Pro Glu
            365             370
Gly Pro Glu Gly Pro Gln Gly Pro Glu Gly Pro Glu
            375             380
Gly Pro Glu Gly Pro Glu Gly Pro Gln Gly Pro Glu
385             390             395
Gly Pro Glu Gly Pro Glu Gly Pro Glu Gly Pro Glu
```

|       |       |       |       |       |       |       |       |       |       |       |
|-------|-------|-------|-------|-------|-------|-------|-------|-------|-------|-------|
|       |       | 400   |       |       |       |       | 405   |       |       |       |

Gly Pro Glu Gly Pro Glu Gly Pro Glu Gly Pro Glu
            410                 415                 420

Gly Pro Gln Gly Pro Glu Gly Pro Glu Gly Pro Glu
                425                     430

Gly Pro Glu Gly Pro Gln Gly Pro Glu Gly Pro Glu
            435                 440

Gly Pro Glu Gly Pro Glu Gly Pro Gln Gly Pro Glu
445             450                     455

Gly Pro Glu Gly Pro Glu Gly Pro Glu Gly Pro Gln
                460                 465

Gly Pro Glu Gly Pro Glu Gly Pro Glu Gly Pro Glu
            470                 475                 480

Gly Pro Gln Gly Pro Glu Gly Pro Glu Gly Pro Glu
                485                         490

Gly Pro Glu Gly Pro Gln Gly Pro Glu Gly Pro Glu
            495                 500

Gly Pro Glu Gly Pro Glu Gly Pro Gln Gly Pro Glu
505             510                     515

Gly Pro Glu Gly Pro Glu Gly Pro Glu Gly Pro Gln
                520                     525

Gly Pro Glu Gly Pro Glu Gly Pro Glu Gly Pro Glu
            530                 535                 540

( 2 ) INFORMATION FOR SEQ ID NO:6:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:6:

Gly Pro Ile Gly Leu Ile Gly Pro Arg Gly Pro Pro
                5                   10

Gly Ala Ser Gly Ala Pro Gly Pro Glu Gly Phe Gln
            15                  20

Gly
25

( 2 ) INFORMATION FOR SEQ ID NO:7:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No (v) FRAGMENT TYPE: Internal (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:7:

Gly Pro Lys Gly Leu Lys Gly Pro Arg Gly Pro Pro
                  5                      10
Gly Ala Ser Gly Ala Pro Gly Pro Glu Gly Phe Gln
            15                  20
Gly
 25

(2) INFORMATION FOR SEQ ID NO:8:

(i) SEQUENCE CHARACTERISTICS:
        (A) LENGTH: 25
        (B) TYPE: Amino acid
        (D) TOPOLOGY: Linear (ii) MOLECULE TYPE: Polypeptide (iii) HYPOTHETICAL: No (iv) ANTI-SENSE: No (v) FRAGMENT TYPE: Internal (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:8:

Gly Pro Asn Gly Leu Asn Gly Pro Arg Gly Pro Pro
                  5                      10
Gly Ala Ser Gly Ala Pro Gly Pro Glu Gly Phe Gln
            15                  20
Gly
 25

(2) INFORMATION FOR SEQ ID NO:9:

(i) SEQUENCE CHARACTERISTICS:
        (A) LENGTH: 25
        (B) TYPE: Amino acid
        (D) TOPOLOGY: Linear (ii) MOLECULE TYPE: Polypeptide (iii) HYPOTHETICAL: No (iv) ANTI-SENSE: No (v) FRAGMENT TYPE: Internal (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:9:

Gly Pro Tyr Gly Leu Tyr Gly Pro Arg Gly Pro Pro
                  5                      10

Gly Ala Ser Gly Ala Pro Gly Pro Glu Gly Phe Gln
                15                      20

Gly
25

( 2 ) INFORMATION FOR SEQ ID NO:10:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:10:

Gly Pro Gln Gly Leu Gln Gly Pro Arg Gly Pro Pro
                5                   10

Gly Ala Ser Gly Ala Pro Gly Pro Glu Gly Phe Gln
                15                      20

Gly
25

( 2 ) INFORMATION FOR SEQ ID NO:11:

( i ) SEQUENCE CHARACTERISTICS:
        ( A ) LENGTH: 25
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:11:

Gly Pro Met Gly Leu Met Gly Pro Arg Gly Pro Pro
                5                   10

Gly Ala Ser Gly Ala Pro Gly Pro Glu Gly Phe Gln
                15                      20

Gly
25

( 2 ) INFORMATION FOR SEQ ID NO:12:

( i ) SEQUENCE CHARACTERISTICS:
        ( A ) LENGTH: 25
        ( B ) TYPE: Amino acid
        ( D ) TOPOLOGY: Linear -continued (ii) MOLECULE TYPE: Polypeptide (iii) HYPOTHETICAL: No (iv) ANTI-SENSE: No (v) FRAGMENT TYPE: Internal (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:12:

Gly Pro His Gly Leu His Gly Pro Arg Gly Pro Pro
                  5                   10
Gly Ala Ser Gly Ala Pro Gly Pro Glu Gly Phe Gln
            15                  20
Gly
25

(2) INFORMATION FOR SEQ ID NO:13:

(i) SEQUENCE CHARACTERISTICS:
    (A) LENGTH: 25
    (B) TYPE: Amino acid
    (D) TOPOLOGY: Linear (ii) MOLECULE TYPE: Polypeptide (iii) HYPOTHETICAL: No (iv) ANTI-SENSE: No (v) FRAGMENT TYPE: Internal (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:13:

Gly Pro Ile Gly Leu Met Gly Pro Arg Gly Pro Pro
                  5                   10
Gly Ala Ser Gly Ala Pro Gly Pro Glu Gly Phe Gln
            15                  20
Gly
25

(2) INFORMATION FOR SEQ ID NO:14:

(i) SEQUENCE CHARACTERISTICS:
    (A) LENGTH: 25
    (B) TYPE: Amino acid
    (D) TOPOLOGY: Linear (ii) MOLECULE TYPE: Polypeptide (iii) HYPOTHETICAL: No (iv) ANTI-SENSE: No (v) FRAGMENT TYPE: Internal (vi) ORIGINAL SOURCE: Synthetically prepared (vii) IMMEDIATE SOURCE: Synthetically prepared (x) PUBLICATION INFORMATION: None ( x i ) SEQUENCE DESCRIPTION: SEQ ID NO:14:

Gly Pro Met Gly Leu Ile Gly Pro Arg Gly Pro Pro
                      5                  10

Gly Ala Ser Gly Ala Pro Gly Pro Glu Gly Phe Gln
             15                  20

Gly
 25

( 2 ) INFORMATION FOR SEQ ID NO:15:

( i ) SEQUENCE CHARACTERISTICS:
         ( A ) LENGTH: 270
         ( B ) TYPE: Amino acid
         ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: Internal ( v i ) ORIGINAL SOURCE: Saccharomyces cerevisiae ( v i i ) IMMEDIATE SOURCE: Saccharomyces cerevisiae ( x ) PUBLICATION INFORMATION: None ( x i ) SEQUENCE DESCRIPTION: SEQ ID NO:15:

Gly Pro Gln Gly Pro Glu Gly Pro Glu Gly Pro Glu
                      5                  10

Gly Pro Glu Gly Pro Gln Gly Pro Glu Gly Pro Glu
             15                  20

Gly Pro Glu Gly Pro Glu Gly Pro Gln Gly Pro Glu
 25                   30                       35

Gly Pro Glu Gly Pro Glu Gly Pro Glu Gly Pro Gln
             40                  45

Gly Pro Glu Gly Pro Glu Gly Pro Glu Gly Pro Glu
 50                   55                       60

Gly Pro Gln Gly Pro Glu Gly Pro Glu Gly Pro Glu
             65                  70

Gly Pro Glu Gly Pro Gln Gly Pro Glu Gly Pro Glu
             75                  80

Gly Pro Glu Gly Pro Glu Gly Pro Gln Gly Pro Glu
 85                   90                       95

Gly Pro Glu Gly Pro Glu Gly Pro Glu Gly Pro Gln
             100                 105

Gly Pro Glu Gly Pro Glu Gly Pro Glu Gly Pro Glu
 110                  115                      120

Gly Pro Gln Gly Pro Glu Gly Pro Glu Gly Pro Glu
             125                 130

Gly Pro Glu Gly Pro Gln Gly Pro Glu Gly Pro Glu
             135                 140

Gly Pro Glu Gly Pro Glu Gly Pro Gln Gly Pro Glu
 145                  150                      155

Gly Pro Glu Gly Pro Glu Gly Pro Glu Gly Pro Gln
             160                 165

Gly Pro Glu Gly Pro Glu Gly Pro Glu Gly Pro Glu
             170                 175                      180

-continued

```
Gly Pro Gln Gly Pro Glu Gly Pro Glu Gly Pro Glu
                185                 190
Gly Pro Glu Gly Pro Gln Gly Pro Glu Gly Pro Glu
            195                 200
Gly Pro Glu Gly Pro Glu Gly Pro Gln Gly Pro Glu
205                 210                 215
Gly Pro Glu Gly Pro Glu Gly Pro Glu Gly Pro Gln
            220                 225
Gly Pro Glu Gly Pro Glu Gly Pro Glu Gly Pro Glu
        230                 235                 240
Gly Pro Gln Gly Pro Glu Gly Pro Glu Gly Pro Glu
                245                 250
Gly Pro Glu Gly Pro Gln Gly Pro Glu Gly Pro Glu
            255                 260
Gly Pro Glu Gly Pro Glu
265                 270
```

( 2 ) INFORMATION FOR SEQ ID NO:16:

( i ) SEQUENCE CHARACTERISTICS:
        ( A ) LENGTH: 543
        ( B ) TYPE: Amino acid
        ( D ) TOPOLOGY: Linear ( i i ) MOLECULE TYPE: Polypeptide ( i i i ) HYPOTHETICAL: No ( i v ) ANTI-SENSE: No ( v ) FRAGMENT TYPE: C-terminal ( v i ) ORIGINAL SOURCE: Saccharomyces cerevisiae ( v i i ) IMMEDIATE SOURCE: Saccharomyces cerevisiae ( x ) PUBLICATION INFORMATION: None ( x i ) SEQUENCE DESCRIPTION: SEQ ID NO:16:

```
Gly Pro Glu Gly Pro Gln Gly Pro Glu Gly Pro Glu
                5                   10
Gly Pro Glu Gly Pro Glu Gly Pro Gln Gly Pro Glu
            15                  20
Gly Pro Glu Gly Pro Glu Gly Pro Glu Gly Pro Gln
25                  30                  35
Gly Pro Glu Gly Pro Glu Gly Pro Glu Gly Pro Glu
            40                  45
Gly Pro Gln Gly Pro Glu Gly Pro Glu Gly Pro Glu
50                  55                          60
Gly Pro Glu Gly Pro Gln Gly Pro Glu Gly Pro Glu
                65                  70
Gly Pro Glu Gly Pro Glu Gly Pro Gln Gly Pro Glu
            75                  80
Gly Pro Glu Gly Pro Glu Gly Pro Glu Gly Pro Gln
85                  90                  95
Gly Pro Glu Gly Pro Glu Gly Pro Glu Gly Pro Glu
            100                 105
Gly Pro Gln Gly Pro Glu Gly Pro Glu Gly Pro Glu
    110                 115                 120
Gly Pro Glu Gly Pro Gln Gly Pro Glu Gly Pro Glu
                125                 130
```

| | | | | | | | | | | |
|---|---|---|---|---|---|---|---|---|---|---|
| Gly | Pro | Glu | Gly | Pro | Glu | Gly | Pro | Gln | Gly | Pro | Glu |
| | | 135 | | | 140 | | | | | | |
| Gly | Pro | Glu | Gly | Pro | Glu | Gly | Pro | Glu | Gly | Pro | Gln |
| 145 | | | | | 150 | | | | | 155 | |
| Gly | Pro | Glu | Gly | Pro | Glu | Gly | Pro | Glu | Gly | Pro | Glu |
| | | | 160 | | | | | 165 | | | |
| Gly | Pro | Gln | Gly | Pro | Glu | Gly | Pro | Glu | Gly | Pro | Glu |
| | | 170 | | | | 175 | | | | | 180 |
| Gly | Pro | Glu | Gly | Pro | Gln | Gly | Pro | Glu | Gly | Pro | Glu |
| | | | | | 185 | | | | 190 | | |
| Gly | Pro | Glu | Gly | Pro | Glu | Gly | Pro | Gln | Gly | Pro | Glu |
| | | 195 | | | | | | 200 | | | |
| Gly | Pro | Glu | Gly | Pro | Glu | Gly | Pro | Glu | Gly | Pro | Gln |
| 205 | | | | | 210 | | | | | 215 | |
| Gly | Pro | Glu | Gly | Pro | Glu | Gly | Pro | Glu | Gly | Pro | Glu |
| | | | 220 | | | | | 225 | | | |
| Gly | Pro | Gln | Gly | Pro | Glu | Gly | Pro | Glu | Gly | Pro | Glu |
| | | 230 | | | | 235 | | | | | 240 |
| Gly | Pro | Glu | Gly | Pro | Gln | Gly | Pro | Glu | Gly | Pro | Glu |
| | | | | | 245 | | | | 250 | | |
| Gly | Pro | Glu | Gly | Pro | Glu | Gly | Pro | Gln | Gly | Pro | Glu |
| | | | | | | | | 260 | | | |
| | | 255 | | | | | | | | | |
| Gly | Pro | Glu | Gly | Pro | Glu | Gly | Pro | Glu | Gly | Pro | Gln |
| 265 | | | | | 270 | | | | | 275 | |
| Gly | Pro | Glu | Gly | Pro | Glu | Gly | Pro | Glu | Gly | Pro | Glu |
| | | | 280 | | | | | 285 | | | |
| Gly | Pro | Gln | Gly | Pro | Glu | Gly | Pro | Glu | Gly | Pro | Glu |
| | | 290 | | | | 295 | | | | | 300 |
| Gly | Pro | Glu | Gly | Pro | Gln | Gly | Pro | Glu | Gly | Pro | Glu |
| | | | | | 305 | | | | 310 | | |
| Gly | Pro | Glu | Gly | Pro | Glu | Gly | Pro | Gln | Gly | Pro | Glu |
| | | 315 | | | | | | 320 | | | |
| Gly | Pro | Glu | Gly | Pro | Glu | Gly | Pro | Glu | Gly | Pro | Gln |
| 325 | | | | | 330 | | | | | 335 | |
| Gly | Pro | Glu | Gly | Pro | Glu | Gly | Pro | Glu | Gly | Pro | Glu |
| | | | 340 | | | | | 345 | | | |
| Gly | Pro | Gln | Gly | Pro | Glu | Gly | Pro | Glu | Gly | Pro | Glu |
| | | 350 | | | | 355 | | | | | 360 |
| Gly | Pro | Glu | Gly | Pro | Gln | Gly | Pro | Glu | Gly | Pro | Glu |
| | | | | | 365 | | | | 370 | | |
| Gly | Pro | Glu | Gly | Pro | Glu | Gly | Pro | Gln | Gly | Pro | Glu |
| | | 375 | | | | | | 380 | | | |
| Gly | Pro | Glu | Gly | Pro | Glu | Gly | Pro | Glu | Gly | Pro | Gln |
| 385 | | | | | 390 | | | | | 395 | |
| Gly | Pro | Glu | Gly | Pro | Glu | Gly | Pro | Glu | Gly | Pro | Glu |
| | | | 400 | | | | | 405 | | | |
| Gly | Pro | Gln | Gly | Pro | Glu | Gly | Pro | Glu | Gly | Pro | Glu |
| | | 410 | | | | 415 | | | | | 420 |
| Gly | Pro | Glu | Gly | Pro | Gln | Gly | Pro | Glu | Gly | Pro | Glu |
| | | | | | 425 | | | | 430 | | |
| Gly | Pro | Glu | Gly | Pro | Glu | Gly | Pro | Gln | Gly | Pro | Glu |
| | | 435 | | | | | | 440 | | | |
| Gly | Pro | Glu | Gly | Pro | Glu | Gly | Pro | Glu | Gly | Pro | Gln |

```
                        445                      450                      455
                Gly    Pro    Glu    Gly    Pro    Glu    Gly    Pro    Glu    Gly    Pro    Glu
                                            460                             465

Gly    Pro    Gln    Gly    Pro    Glu    Gly    Pro    Glu    Gly    Pro    Glu
                             470                             475                             480

Gly    Pro    Glu    Gly    Pro    Gln    Gly    Pro    Glu    Gly    Pro    Glu
                                            485                             490

Gly    Pro    Glu    Gly    Pro    Glu    Gly    Pro    Gln    Gly    Pro    Glu
                             495                             500

Gly    Pro    Glu    Gly    Pro    Glu    Gly    Pro    Glu    Gly    Pro    Gln
                505                             510                             515

Gly    Pro    Glu    Gly    Pro    Glu    Gly    Pro    Glu    Gly    Pro    Glu
                                            520                             525

Gly    Pro    Gln    Gly    Pro    Glu    Gly    Pro    Glu    Gly    Pro    Glu
                             530                             535                             540

Gly    Pro    Glu
```

( 2 ) INFORMATION FOR SEQ ID NO:17:

( i ) SEQUENCE CHARACTERISTICS:
        ( A ) LENGTH: 109 nucleotides
        ( B ) TYPE: Nucleic acid
        ( C ) STRANDEDNESS: Single
        ( D ) TOPOLOGY: Linear ( i i ) MOLECULE TYPE: Encoding DNA strand ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:17:

```
AATTCGGTCC  CGAGGGTCCA  CAAGGTCCAG  AAGGTCCAGA                    40

AGGTCCAGAA  GGTCCAGAAG  GTCCACAAGG  TCCAGAAGGT                    80

CCAGAAGGTC  CAGAAGGTCC  CGAGCTAAG                               109
```

( 2 ) INFORMATION FOR SEQ ID NO:18:

( i ) SEQUENCE CHARACTERISTICS:
        ( A ) LENGTH: 109 nucleotides
        ( B ) TYPE: Nucleic acid
        ( C ) STRANDEDNESS: Single
        ( D ) TOPOLOGY: Linear ( i i ) MOLECULE TYPE: Encoding DNA strand ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:18:

```
TCGACTTAGC  TCGGGACCTT  CTGGACCTTC  TGGACCTTCT                    40

GGACCTTGTG  GACCTTCTGG  ACCTTCTGGA  CCTTCTGGAC                    80
```

```
CTTCTGGACC TTGTGGACCC TCGGGACCG                                                    109
```

(2) INFORMATION FOR SEQ ID NO:19:

(i) SEQUENCE CHARACTERISTICS:
        (A) LENGTH: 105
        (B) TYPE: Amino acid
        (D) TOPOLOGY: Linear (ii) MOLECULE TYPE: Polypeptide (iii) HYPOTHETICAL: No (iv) ANTI-SENSE: No (v) FRAGMENT TYPE: C-terminal (vi) ORIGINAL SOURCE: Saccharomyces cerevisiae (vii) IMMEDIATE SOURCE: Saccharomyces cerevisiae (x) PUBLICATION INFORMATION: None (xi) SEQUENCE DESCRIPTION: SEQ ID NO:19:

```
Asp Tyr Lys Asp Asp Asp Asp Lys Glu Phe Gly Lys
                 5                   10
Gly Pro Glu Gly Pro Gln Gly Pro Glu
         15                  20
Gly Pro Glu Gly Pro Glu Gly Pro Glu Gly Pro Gln
             25                  30
Gly Pro Glu Gly Pro Glu Gly Pro Glu Gly Pro Glu
         35              40                  45
Gly Pro Gln Gly Pro Glu Gly Pro Glu Gly Pro Glu
                 50                  55
Gly Pro Glu Gly Pro Gln Gly Pro Glu Gly Pro Gln
             60                  65
Gly Pro Glu Gly Pro Glu Gly Pro Gln Gly Pro Glu
    70              75                  80
Gly Pro Glu Gly Pro Glu Gly Pro Glu Gly Pro Gln
             85                  90
Gly Pro Glu Gly Pro Glu Gly Pro Glu Gly Pro Glu
    95                  100                 105
```

(2) INFORMATION FOR SEQ ID NO:20:

(i) SEQUENCE CHARACTERISTICS:
        (A) LENGTH: 285
        (B) TYPE: Amino acid
        (D) TOPOLOGY: Linear (ii) MOLECULE TYPE: Polypeptide (iii) HYPOTHETICAL: No (iv) ANTI-SENSE: No (v) FRAGMENT TYPE: C-terminal (vi) ORIGINAL SOURCE: Saccharomyces cerevisiae (vii) IMMEDIATE SOURCE: Saccharomyces cerevisiae (x) PUBLICATION INFORMATION: None (xi) SEQUENCE DESCRIPTION: SEQ ID NO:20:

```
Asp Tyr Lys Asp Asp Asp Asp Lys Glu Phe Gly Lys
                 5                   10
```

-continued

```
Gly Pro Glu Gly Pro Gln Gly Pro Glu Gly Pro Glu
         15                  20
Gly Pro Glu Gly Pro Glu Gly Pro Gln Gly Pro Glu
 25              30                      35
Gly Pro Glu Gly Pro Glu Gly Pro Glu Gly Pro Gln
             40                  45
Gly Pro Glu Gly Pro Glu Gly Pro Glu Gly Pro Glu
         50              55                      60
Gly Pro Gln Gly Pro Glu Gly Pro Glu Gly Pro Glu
             65                  70
Gly Pro Glu Gly Pro Gln Gly Pro Glu Gly Pro Glu
         75                  80
Gly Pro Glu Gly Pro Glu Gly Pro Gln Gly Pro Glu
 85              90                      95
Gly Pro Glu Gly Pro Glu Gly Pro Glu Gly Pro Gln
             100                 105
Gly Pro Glu Gly Pro Glu Gly Pro Glu Gly Pro Glu
         110             115                     120
Gly Pro Gln Gly Pro Glu Gly Pro Glu Gly Pro Glu
             125                 130
Gly Pro Glu Gly Pro Gln Gly Pro Glu Gly Pro Glu
         135                 140
Gly Pro Glu Gly Pro Glu Gly Pro Gln Gly Pro Glu
145             150                     155
Gly Pro Glu Gly Pro Glu Gly Pro Glu Gly Pro Gln
             160                 165
Gly Pro Glu Gly Pro Glu Gly Pro Glu Gly Pro Glu
         170             175                     180
Gly Pro Gln Gly Pro Glu Gly Pro Glu Gly Pro Glu
             185                 190
Gly Pro Glu Gly Pro Gln Gly Pro Glu Gly Pro Glu
         195                 200
Gly Pro Glu Gly Pro Glu Gly Pro Gln Gly Pro Glu
205             210                     215
Gly Pro Glu Gly Pro Glu Gly Pro Glu Gly Pro Gln
             220                 225
Gly Pro Glu Gly Pro Glu Gly Pro Glu Gly Pro Glu
         230             235                     240
Gly Pro Gln Gly Pro Glu Gly Pro Glu Gly Pro Glu
             245                 250
Gly Pro Glu Gly Pro Gln Gly Pro Glu Gly Pro Glu
         255                 260
Gly Pro Glu Gly Pro Glu Gly Pro Gln Gly Pro Glu
265             270                     275
Gly Pro Glu Gly Pro Glu Gly Pro Glu
             280                 285
```

COLLAGEN-LIKE POLYPEPTIDES AND BIOPOLYMERS AND NUCLEIC ACIDS ENCODING SAME

This is a Divisional of U.S. application Ser. No. 08/383,804, filed Feb. 3, 1995, now U.S. Pat. No. 5,670,616.

FIELD OF THE INVENTION

This invention relates to polypeptides and biopolymers which have collagen-like properties and can be used, for example, as silver halide nucleation or growth peptizers in making photographic emulsions. This invention also relates to recombinant expression vectors, host cells and nucleic acids useful for making the noted biopolymers.

BACKGROUND OF THE INVENTION

Recombinant DNA technology has been applied in the isolation of natural genes and the expression of those genes in host cells. In addition, it has been used to produce modified proteins using modified genes, or combinations of portions of natural genes. Briefly, such proceedures include: (1) isolation and purification (or chemical synthesis) of a specific gene or gene segment containing the genetically coded information for the amino acid sequence of the desired protein or polypeptide, (2) recombination of the gene segment with an appropriate transfer vector, and (.3) transfer of the modified vector to the appropriate host cell for expression of the protein or polypeptide.

With the advent of efficient and automated methods for chemical synthesis of DNA, it has become possible to synthesize entire genes and to modify them during synthesis. Most of these attempts have been directed to the production of natural or modified versions of the natural polypeptides. Less attempts have been made to use the technology to produce entirely new polypeptides.

Beginning in the early 1980's, however, researchers began publishing and patenting new approaches to the use of recombinant technology to product new proteins, or "biopolymers" as they are conventionally known. Many genes have been cloned and expressed from plasmid vectors for production of enzymes, antibodies and other proteins which have various physiological functions. Yet, fewer genes have been cloned that code for all or part of structural proteins such as components of the extracellular matrix in multicellular higher organisms. Such proteins are the subject of growing interest, and include collagens, elastin, fibrinectin and other fibrous proteins.

Some early work to produce structural proteins is described in U.S. Pat. No. 5,243,038 (Ferrari et al) relating to high molecular weight recombinant polypeptides having repetitive oligomeric units. Some of the described proteins have the same composition and physical properties of certain silks and were produced using Escherichia coli host cells.

Various reseachers, such as Tirrell et al [MRS BulletinI, XVI(7), 22–28, 1991], have described their efforts to make polymeric materials using recombinant DNA techniques, as well as the considerable problems that must be overcome for success in this field of work.

Certain small (100 amino acid) collagen-like biopolymers (containing repeating glycine-proline-proline amino acids) are described in U.S. Pat. No. 5,089,406 (Williams et al), but the described materials are genetically unstable because of recombination of the DNA into altered sequences.

WO-A-90/05177 (published May 17, 1990) describes the synthesis of synthetic proteins which have properties similar to silk, elastin, keratin and collagen from E. coli. The proteins have various components which provide various functions in a given environment.

Other synthetic structural proteins are described in WO-A-92/09695 (published Jun. 11, 1992), and collagen-like materials were produced by Goldberg et al (Gene, 80, 305–314, 1989) using E. coli. Goldberg et al noted (Page 310) that the polypeptide they produced by intracellular means degraded (80%) in only 40 minutes under modest heat (41° C.).

FR-A-2,685,347 (published Jun. 26, 1993) describes the preparation of recombinant peptides as substitutes for gelatin having diverse uses. The described peptides are considered similar to type I bovine collagen, were prepared using E. coli host cells, and are alleged to represent an improvement in homogeneity for their use in holography. The specific peptides contain many triplets of the amino acids glycine-proline-alanine alternating with triplets of the amino acids glycine-glutamic acid-arginine. Histidine triplets are specifically included in the peptides to provide affinity for a nickel-NTA-agarose recovery resin, and a methionine is included between the histidine triplets and other triplets to permit chemical degradation so that only the non-histidine triplets are retained in the final product. A cysteine is included for binding to chromatographic resins or proteins, and a leucine is placed critically between the methionine and histidine because of its restriction site. Thus, the polypeptides have a complicated sequence of amino acids, particularly on one end, for capture and recovery of the desired material. The actual usefulness of the described materials is not demonstrated in the noted publication.

Such materials are believed to have a low expression yield, that is often the level of expression is so low as to be detectable only using radioactive labeling of the cells, or antibodies specific to a particular tag or peptide sequence. The preparation of these materials is lengthy and tedious, requiring a costly purification procedure from cell paste lysates. Because of the low expression level, the production yield is also low. Because of the particular described capture mode, the removal of epitopic affinity tags by chemical or enzymatic means is tedious and costly with no certainty of complete removal. Thus, some of the molecules have extraneous amino acids which are not part of the desired collagen-like sequence.

There remains a need for collagen-type polypeptides prepared using recombinant DNA techniques which are well designed for useful technological applications and which are convenient for large scale industrial production and purification procedures. Moreover, it would be useful to have polypeptides which behave similarly to gelatin which do not require complicated amino acid sequences for recovery or purification.

SUMMARY OF THE INVENTION

The present invention overcomes problems of known materials by providing a polypeptide comprising the peptide sequence represented by the formula:

I:
$\{[(Gly\ Pro\ Gln)(Gly\ Pro\ Glu)_4]_2\}_n$
II:
$Gly\ Pro\ Glu\{[(Gly\ Pro\ Gln)(Gly\ Pro\ Glu)_4]_2\}_n$
III:
Gly Pro Xaa$_1$ Gly Leu Xaa$_2$ Gly Pro Arg Gly Pro Pro
Gly Ala Ser Gly Ala Pro Gly Pro Glu Gly Phe Gln Gly wherein $X_1$ and $X_2$ are independently the amino acids identified as M, I, H, K, N, Y or Q, and n is 1 to 25.

This invention also provides a recombinant nucleic acid having as at least part of its sequence, a nucleotide sequence which encodes the peptide sequence described above, or its nucleotide complement.

Further, a recombinant biopolymer of this invention comprises at least one occurrence of the peptide sequence represented by formula I, II or III noted above.

Still further, this invention provides a recombinant vector comprising a nucleic acid having as part of its sequence, a nucleotide sequence which encodes the recombinant biopolymer described above, or its nucleotide complement. A suitable host cell can include a recombinant vector comprising the noted nucleic acid wherein the nucleic acid is operationally linked to nucleic acid sequences which allow expression of the nucleic acid in the host cell.

The polypeptides and biopolymers of this invention have properties like bovine collagen, and can be used, for example, to control the nucleation and growth of silver halide grains in the making of photographic emulsions. In particular, the biopolymers can be chosen to provide a specific type of silver halide morphology (size and shape) more uniformly. However, the uses of the present invention are not limited to the preparation of photographic emulsions, but have other uses as noted below. The polypeptides of this invention have uniformity which is not normally possible with conventional synthetic methods, and the sites and properties are controllable.

The polypeptides of this invention may be used as ion-framework polymers having organized stretches of hydrogen bond acceptors, donors or surface charges. Such polymers provide complementary ordered water molecules, electrostatic fields or ion-hole topography at the second and higher order counter ion condensation layers to organize assemblies of silver halide ion clusters into silver halide crystal nuclei.

DETAILED DESCRIPTION OF THE INVENTION

Figure 1A:
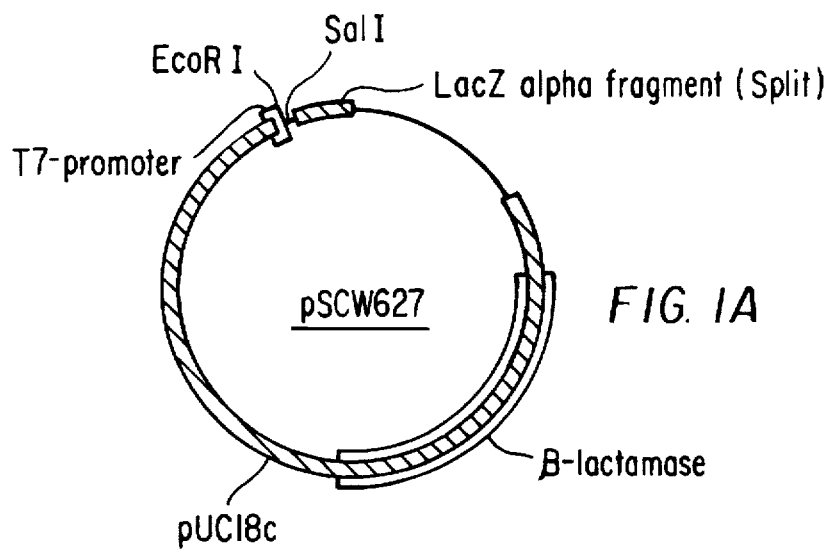
FIG. 1A, 1B and 1C are diagrams of cloning plasmids used in the recombinant preparation of one embodiment of the present invention, as described in Example 1 below.

The polypeptides, biopolymers or nucleic acids of this invention are not known to occur in nature in an isolated state.

The term "polypeptide" is used herein to refer to sequences having at least 20 amino acids, such sequences having at least one occurrence of one or more of the peptide sequences identified herein as formulae I, II and III, or a tripeptide contained in these three peptide sequences.

The terms "biopolymer" and "protein" are used interchangeably and are meant to refer to molecules having more amino acids than the specific polypeptides of this invention, but including at least one of those polypeptides.

"Binding affinity for silver" refers to a measure of the capacity of a given polypeptide or biopolymer to bind with silver ion. It is determined by measuring the differences in silver potential ($\Delta$ vAg) between that of a phosphate buffer solution (pH 7.0) of silver nitrate ($5 \times 10^{-6}$ molar), potassium nitrate (0.1 molar) and the polypeptide or biopolymer (0.3 weight %), compared to a similar solution without the polypeptide or biopolymer. Potential is measured using a bare silver electrode against a silver/silver chloride reference electrode in a salt bridge assembly.

"Low binding affinity" is defined as a $\Delta$ vAg of 50 mV or less. "High binding affinity" is defined as a $\Delta$ vAg of greater than 50 mV.

Amino acids are described herein by the conventional three-letter symbol, and nucleotides are identified using the conventional single-letter symbol for the individual bases.

As noted above, the polypeptides of this invention can be used to control the nucleation and growth of silver halide grains, and thereby to provide improved photographic emulsions. A demonstration of such utility is shown in Example 3 below.

However, the biopolymers of this invention have potential use as biosensors, binders for drug delivery systems, as non-allergenic materials for human plastic surgery, as linear electron accelerating conducting wires for what are known as "biochips" (see for example, U.S. Pat. No. 4,764,415), as core structure elements for organizing dyes three dimensionally for non-linear optic elements, as uranium salt recovery materials, and as peptide food additives.

The polypeptides of this invention have one of the following peptide sequences represented as formulae I, II or III:

I:
{[(Gly Pro Gln)(Gly Pro Glu)$_4$]$_2$}$_n$
II:
Gly Pro Glu{[(Gly Pro Gln)(Gly Pro Glu)$_4$]$_2$}$_n$
III:
Gly Pro Xaa$_1$ Gly Leu Xaa$_2$ Gly Pro Arg Gly Pro Pro Gly Ala Ser Gly Ala Pro Gly Pro Glu Gly Phe Gln Gly wherein Xaa$_1$ and Xaa$_2$ are independently the amino acids identified as Met, Ile, His, Lys, Asn, Tyr or Gln, and n is 1 to 25.

In the foregoing peptide sequences of formulae I and II, it is preferred that n is 3 to 20, and more preferred that n be from 3 to 18.

In one embodiment, Xaa$_1$ and Xaa$_2$ in peptide sequence of formulae III are the same amino acids, such as Ile, Lly, Asn, Tyr or Gln. Most preferably, each of Xaa$_1$ and Xaa$_2$ is Gln. The polypeptides of this embodiment generally have a low binding affinity for silver ion, and thus are particularly useful for preparing thin tabular grains (as described below in Example 3. Other biopolymers having a low binding affinity for silver ion include peptide sequences of formulae I and II wherein n is 3 to 18.

In a second embodiment, useful polypeptides having peptide sequence of formulae III have Met or His for both of Xaa$_1$ and Xaa$_2$.

In a third embodiment, useful biopolymers have peptide sequence of formulae III is such that Xaa$_1$ is Ile and Xaa$_2$ is Met, or Xaa$_1$ is Met and Xaa$_2$ is Ile.

The polypeptides of the second and third embodiments generally have a high binding affinity for silver ion, and thus are particularly useful for preparing silver halide emulsions having non-tabular morphologies (such as octahedral or irregular).

Particularly useful peptide sequences or biopolymers of this invention include:

SEQ ID NO: 1:
Gly Pro Glu {[(Gly Pro Gln)(Gly Pro Glu)$_4$]$_2$}$_3$
SEQ ID NO: 2:
Gly Pro Glu {[(Gly Pro Gln)(Gly Pro Glu)$_4$]$_2$}$_4$
SEQ ID NO: 3:
Gly Pro Glu {[(Gly Pro Gln)(Gly Pro Glu)$_4$]$_2$}$_9$
SEQ ID NO: 4:
{[(Gly Pro Gln)(Gly Pro Glu)$_4$]$_2$}$_1$
SEQ ID NO: 5:
{[(Gly Pro Gln)(Gly Pro Glu)$_4$]$_2$}$_{18}$
SEQ ID NO: 6:
Gly Pro Ile Gly Leu Ile Gly Pro Arg Gly Pro Pro Gly Ala Ser Gly Ala Pro Gly Pro Glu Gly Phe Gln Gly
SEQ. ID NO: 7:
Gly Pro Lys Gly Leu Lys Gly Pro Arg Gly Pro Pro Gly Ala Ser Gly Ala Pro Gly Pro Glu Gly Phe Gln Gly
SEQ ID NO: 8:
Gly Pro Asn Gly Leu Asn Gly Pro Arg Gly Pro Pro Gly Ala Ser Gly Ala Pro Gly Pro Glu Gly Phe Gln Gly
SEQ ID NO: 9:
Gly Pro Tyr Gly Leu Tyr Gly Pro Arg Gly Pro Pro Gly Ala Ser Gly Ala Pro Gly Pro Glu Gly Phe Gln Gly
SEQ ID NO: 10:
Gly Pro Gln Gly Leu Gln Gly Pro Arg Gly Pro Pro Gly Ala Ser Gly Ala Pro Gly Pro Glu Gly Phe Gln Gly
SEQ ID NO: 11:
Gly Pro Met Gly Leu Met Gly Pro Arg Gly Pro Pro Gly Ala Ser Gly Ala Pro Gly Pro Glu Gly Phe Gln Gly
SEQ ID NO: 12:
Gly Pro His Gly Leu His Gly Pro Arg Gly Pro Pro Gly Ala Ser Gly Ala Pro Gly Pro Glu Gly Phe Gln Gly
SEQ ID NO: 13:
Gly Pro Ile Gly Leu Met Gly Pro Arg Gly Pro Pro Gly Ala Ser Gly Ala Pro Gly Pro Glu Gly Phe Gln Gly
SEQ ID NO: 14:
Gly Pro Met Gly Leu Ile Gly Pro Arg Gly Pro Pro Gly Ala Ser Gly Ala Pro Gly Pro Glu Gly Phe Gln Gly
SEQ ID NO: 15:
{[(Gly Pro Gln)(Gly Pro Glu)$_4$]$_2$}$_9$
and
SEQ ID NO: 16:
Gly Pro Glu {[(Gly Pro Gln)(Gly Pro Glu)$_4$]$_2$}$_{18}$ A most preferred polypeptide has the peptide sequence identified above as SEQ ID NO:15.

The polypeptides of this invention can be used as isolated peptide sequences, or they can be included as polypeptide sequences of biopolymers. Thus, the biopolymers of this invention can have one or more occurrences of one or more of the noted peptide sequences, or any combination thereof. More particularly, such biopolymers generally have multiple occurrences of the peptide sequences, for example, at least 3 and up to 25 occurrences. Moreover, the biopolymers can have one or more occurrences of a combination of two or more of the noted peptide sequences.

The biopolymers of the present invention can be prepared in a number of ways. Specific details of preparatory methods are presented in Examples 1 and 2 below.

For example, they can be prepared using conventional fMoc peptide synthesis, as described in *Synthetic Peptides: A User's Guide*, W. H. Freeman, Inc., 1992. Thus, the polypeptides were prepared using these techniques, including purification to greater than 99.7% full length purity by reverse phase high performance liquid chromatography. The identity of the purified biopolymer can be confirmed by amino acid analysis. The usual amounts of biopolymers prepared in this manner is on the order of a few milligrams up to a few grams. This chemical synthetic procedure is described in more detail in Example 2 below.

The biopolymers can also be prepared using conventional DNA recombinant techniques (consider, for example, *Recombinant DNA*, 2nd Ed., W. H. Freeman, Inc., 1992, *Molecular Cloning: A Laboratory Manual*, 2nd Ed., Vols. I, II and III, Cold Spring Harbor Press, 1989, *Guide to Molecular Cloning Techniques, Methods in Enzymolocry*, Vol. 152, Academic Press, Inc., 1987, *Guide to Yeast Genetics and Molecular Biology, Methods in Enzymology*, Vol. 194, Academic Press, Inc., 1991 among many other well known textbooks and journal publications). Conventional protein expression procedures using various bacterial or yeast host cells can be practiced, as well as conventional purification techniques. The host cells typically containing a recombinant vector which comprises the nucleic acid of interest operationally linked to nucleic acid sequences which allow expression of the desired polypeptide in the host cells.

Further, the biopolymers can be prepared using a novel preparatory procedure which is described below in general terms, and in more detail in Example 1 below. This novel approach involves the use of baker's yeast, *Saccharomyces cerevisiae*, as the host cell for polypeptide expression, in the presence or absence of an N-terminus eight amino acid epitope (identified as the FLAG™ epitope, owned by Immunex Corp. and described more fully by Hopp et al, *Biotechnology*, 6, 1204–1210, 1988) and several additional amino acids including a proteolytic trypsin site for cleavage removal at a particular lysine.

This invention also provides recombinant nucleic acid, vectors and plasmids which have as at least part of their sequences, a nucleotide sequence which encodes for the peptide sequences, polypeptides or biopolymers of the present invention. Obviously, one skilled in the art, knowing the particular sequence of amino acids that is desired, would readily be able to design the particular nucleotide sequence encoding therefor. Because of the known degeneracy of the genetic code, various codons can-be included in a nucleic acid to provide expression of the desired peptide sequence or biopolymer. There are a number of techniques known in the art to determine which codons are preferred to provide optimum expression. Such optimization may be largely empirical and tedious, but it is generally not complex or difficult to accomplish. It is known, however, that alteration of codons at the beginning (within the first few codons) of a gene can enhance expression efficiency in certain host cells.

Besides the peptide sequences described herein, the biopolymers of the present invention can also include specific amino acids which provide sites for cleavage by various enzymes (for example, endoproteases) to provide desired fragments, and specific sequences which provide antibody affinity to the biopolymer to aid in purification techniques, metal chelation or hydroxyapatite purification, to confer biopolymer stability, to enhance expression is specific host cells, to provide flavor or therapeutic or analgesic effects, or to deliver drugs. Thus, the synthetic structural biopolymers of this invention can be used not only for the conventional uses common to structural proteins, but to provide a matrix or carrier for many other in vivo or in vitro biological, medicinal and therapeutic uses, as well as the food and environmental treatment industries.

The biopolymers described herein can be identified by staining from contact with a carbocyanine dye, particularly a cationic carbocyanine dye, such as 4,5,4',5'-dibenzo-3,3'-diethyl-9-methyl-thiacarbocyanine bromide, under suitable conditions. Other useful dyes and appropriate staining conditions would be readily apparent to a skilled worker in the art.

The following examples are included to illustrate the practice of this invention, and are not to be used to limit its scope. All percentages are by weight, unless otherwise indicated.

EXAMPLE 1

Recombinant DNA Preparation and Purification of Biopolymer

This example demonstrates a preferred method for preparing a biopolymer of this invention. Specifically, it illustrates the use of *Saccharomyces cerevisiae* (*S. cerevisiae*) as the host organism to prepare the polypeptide (or biopolymer) identified herein as SEQ ID NO:3. This biopolymer comprises the amino acid sequence "Gly Pro Glu" followed by 9 replicates of the polypeptide sequence SEQ ID NO:4, also identified herein as the "GG monomer".

To prepare a double strand nucleic acid that encodes the GG monomer, a sequence with optimum codon usage for *S. cerevisiae* was chosen. Two complementary DNA oligonucleotides encoding the GG monomer were chemically synthesized by standard automated trityl phosphoamidate reactions (F. Eckstein, *Oligonucleotide and Analogs*, Oxford University Press, Oxford, England, 1991). The top strand was the encoding strand. Additional sequences needed for cloning of the hybridized oligonucleotides and the directional assembly of the DNA fragments into DNA concatenated polymers that code for biopolymers are also included in these oligonucleotides (as described below).

The top strand oligonucleotide had the sequence:

SEQ ID NO: 17

5'-AATTCGGTCC CGAGGGTCCA CAAGGTCCAG

AAGGTCCAGA AGGTCCAGAA GGTCCAGAAG

GTCCACAAGG TCCAGAAGGT CCAGAAGGTC

CAGAAGGTCC CGAGCTAAG-3'

The complementary bottom strand oligonucleotide had the sequence:

SEQ ID NO: 18

5'-TCGACTTAGC TCGGGACCTT CTGGACCTTC

TGGACCTTCT GGACCTTGTG GACCTTCTGG

ACCTTCTGGA CCTTCTGGAC CTTCTGGACC

TTGTGGACCC TCGGGACCG-3'

Inside the ends of these two oligonucleotides were encoded Ava I nonpalindromic restriction sites (underlined in SEQ ID NO:17) which, upon proper manipulation, oriented the directional assembly of DNA fragments into repeated head-to-tail DNA concatamers, encoding repeated biopolymers. For SEQ ID NO:3 biopolymer, the form of the Ava I site chosen was:

| top strand: | CCCGAG |
| bottom strand: | GGGCTC |

This Ava I sequentially encoded a pro-glu dipeptide which is part of the desired polypeptide sequence. Upon assembly of this fragment into an array of repeated DNA fragments, the result was a perfect coding for the biopolymer with no amino acids other than those in the noted GG monomer sequence.

The two oligonucleotides, upon hybridization, formed a double stranded nucleic acid having cohesive ("sticky") ends for the restriction sites Eco RI and Sal I. Hybridization was carried out in a solution of tris(hydroxymethyl) aminomethane buffer (10 mmolar, pH 8), containing ethylenediaminetetraacetic acid (1 mmolar) and the oligonucleotides (20 μg/ml of each). Hybridization was begun at 950° C., and the reaction mixture was gradually cooled to 25° C. at a rate of 1° C./15 minutes. Hybridization was determined to be successful by analysis for the presence of a single narrow band of the correct double strand molecular weight upon electrophoresis in a conventional 6% polyacrylamide gel [using tris(hydroxymethyl)-aminomethane, borate and ethylenediaminetetraacetic acid], or by a cooperative thermal denaturation observed by a hyperchromic increase in absorbance at 260 nm.

Figure 1B:
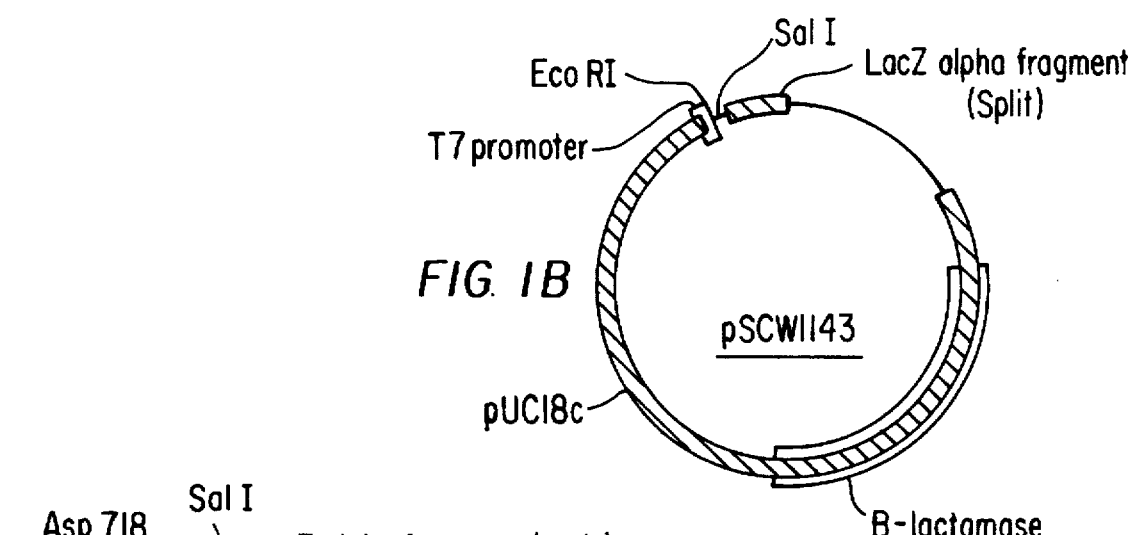
Figure 1C:
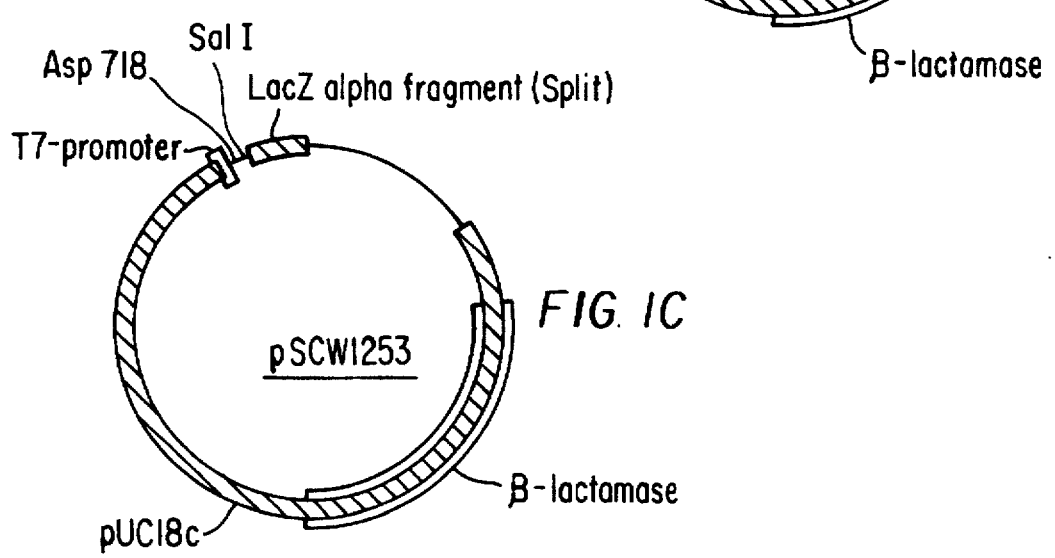

This hybridized fragment was then ligated into the Eco RI and Sal I sites of a modified derivative of the commercially available pTZ18R Genescribe plasmid that has a shortened polylinker consisting of Eco RI, Ava I, Sal I, Hind III (pSCW627), as shown in FIG. 1. This and other modified pTZ18R Genescribe derivatives are biopolymer cloning vectors, because this is where monomer DNA or repeated multimers are cloned after oligonucleotide hybridization (cloning of what is identified as "GG monomer DNA") or directional assembly (cloning of "multimer GG" DNA). Three such cloning vectors are pSCW627, pSCW1143, pSCW1253, as shown in-FIGS. 1A 1B and 1C. The plasmid pSCW627 was used for cloning the Eco RI-Sal I hybridized oligonucleotide pair, whereas pSCW1143 was used for the cloning of repeated GG monomer DNA to produce DNA encoding for the amino acid sequence Glu Phe Gly Lys Gly Pro Glu {[(Gly Pro Gln)(Gly Pro Glu)$_4$]$_2$}$_n$ wherein the underlined Lys is the lysine that ultimately will be cleaved in the biopolymer by Trypsin to remove the N-terminal FLAG™ epitope (the Asp Tyr Lys (Asp)$_4$ Lys FLAG™ epitope sequence is encoded by the yeast expression plasmid]. The N-terminal FLAG™ epitope generally provides for analytical detection by conventional anti-FLAG® monoclonal antibodies, $M_1$ or $M_2$, to the [Asp Tyr Lys (Asp)$_4$ Lys] FLAG™ epitope sequence in conjunction with the use of conventional Western blots.

Plasmid pSCW1253 was used for the "landing" of repeated GG monomer DNA that ultimately was used to secrete the biopolymer sequence SEQ ID NO:22 devoid of the presence of any nonpolymer amino acids as used in pSCW1143 constructions (that is, the N-terminal FLAG™ epitope from the yeast expression plasmid, the amino acids encoded by the restriction enzyme site, Eco RI, and the Gly-Lys dipeptide for Trypsin cleavage).

The assembly of repetitive DNA monomers was separated into repeating multimers, and the potential recombination toxicity of direct repeats of DNA was. separated from the actual production of the secreted amino acid biopolymer and the potential protein toxicity to the cell by using two different organisms (a prokaryote and an eukaryote). First, the repetitive DNA was initially cloned in *E. coli* with the reading frame of the inserts out of the reading frame of lacZ in the vectors pSCW627, pSCW1143 and pSCW1253. Second, the biopolymer was produced by secretion in the baker's yeast, *S. cerevisiae*.

A mixture of the hybridized GG monomer DNA as described above was ligated into the Eco RI and Sal I sites of pSCW627 with T4 DNA ligase at 16° C. for 16 hours by standard methods. The ligation reaction was then transformed into *E. coli* strain JM109 [genotype el4–(mcrA), recA1, endA1, gyrA96, thi–1, hsdR17($r_{k-}$, $m_{k+}$), supE44, relA1, Δ(lac-proAB), (F'traD36, proAB, lacI$^q$zΔM15)] that had been made competent by a standard calcium chloride procedure and stored at −80° C. (see *Molecular Cloning: A Laboratory Manual*, noted above). The transformation reaction was plated onto X-GAL (80 µg/ml) LB plus ampicillin (150 µg/ml) plates and incubated at 37° C. Transformants were picked into liquid LB plus ampicillin media, grown overnight at 37° C., and plasmid DNA prepared by standard methods.

The presence of clones containing inserts was analyzed by Eco RI-Sal I double digests and by Ava I solo digests. Clones containing the hybridized oligonucleotide insert were white, because the oligonucleotide Eco RI-Sal I fragment has an in-frame stop codon included between the last Ava I site and the Sal I site, which ensures a convenient X-GAL blue/white color transformation assay for the presence of the hybridized GG monomer.

A monomer fragment called "AG monomer", in which the encoded glutamines had been replaced by encoded asparagines, was also cloned in parallel.

Figure 2A:
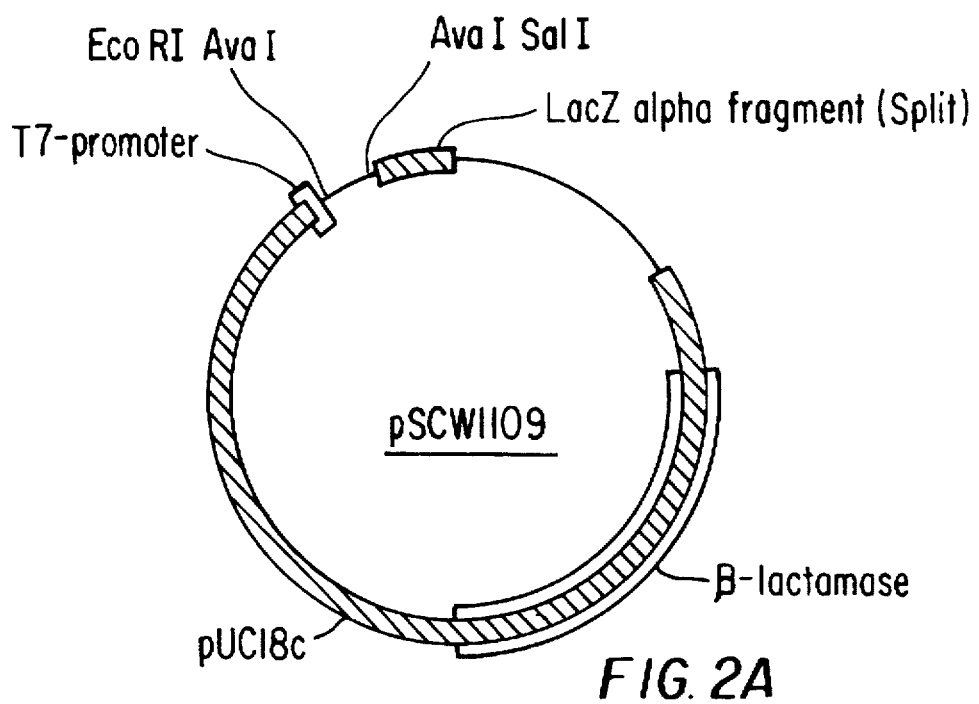
FIGS. 2A and 2B are schematic diagrams of certain "monomer plasmids" used in the recombinant preparation of one embodiment of the present invention, as described in Example 1 below.
Figure 2B:
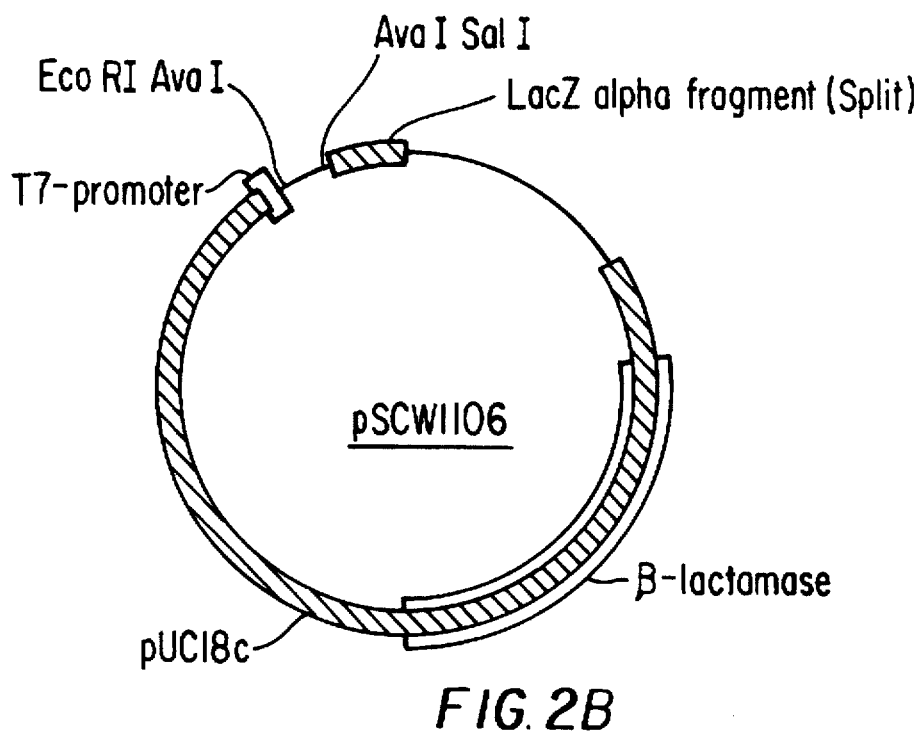

Two plasmids, pSCW1109 and pSCW1106 (see FIG. 2) were found to have putative monomer inserts of GG monomer and AG monomer, respectively, of the correct size, as determined using gel electrophoresis and conventional molecular weight markers. No evidence of plasmid instability due to recombination of the GG monomer or AG monomer inserts was observed.

The GG and AG monomers encoded in the two plasmids, pSCW1109 and pSCW1106, respectively, were found to match the desired encoded monomer sequence as determined by fluorescent DNA sequencing on a conventional Applied Biosystems 390 instrument using standard procedures.

The sequenced GG monomer DNA, inserted into pSCW627 and identified as pSCW1109 DNA is shown as follows in Schematic 1:

as determined from the presence of two bands at 90 bp and 2.9 kbp on a conventional agarose gel. The Ava I monomer DNA was separated from the plasmid backbone by preparative 2% w/v agarose electrophoresis using a buffered solution containing tris(hydroxymethyl)aminomethane, phosphate and ethylenediaminetetraacetic acid, and visualized by ethidium bromoiodide staining and fluorescence. The agarose strip containing the Ava I monomer DNA was cut out of the gel and purified by a glass milk procedure using US BIOCLEAN™ glass beads (available from US Biochemicals, Inc.) according to the instructions provided.

Multimers of the GG monomer (identified herein as "GG multimers") were prepared by self legating the GG monomer DNA with T4 DNA ligase under standard conditions at 16° C. until a distribution of polymer repeats from 2 to greater than 40 occurred, as determined by 0.7% w/v agarose electrophoresis. Size fractionated GG multimers were prepared: first, by separation on a preparative 0.7% agarose electrophoresis gel, secondly, by visualizing the bands by ethidium bromide staining and fluorescence, and thirdly, by cutting the multimer ladder distribution into agarose slices, each containing a given size pool of repeats of GG monomer, (3 to 6, 7 to 11, 12 to 17, 18 to 24, 25 to 33 and lastly to the top of the multimer distribution). Finally, each multimer DNA pool was purified from the agarose gel slice by the glass milk procedure (noted above).

Each size fractionated GG multimer pool was ligated by standard procedures at 16° C. overnight with T4 DNA ligase into pSCW1143 or pSCWl253 at the Ava I site (FIG.; 1B and 1C) which had been dephosphorylated by standard procedures with calf intestinal phosphatase or shrimp alkaline phosphatase. Dephosphorylation insures a greater percentage of insert containing transformants when a single restriction site is used for cloning.

To produce the GG biopolymer having a FLAG™ epitope that is removable by Trypsin, the landing plasmid pSCW1143 is used. The plasmid encodes a lysine Trypsin cleavage site. Schematic 2 below (pSCW1143 linker) shows the reading frame that results from cloning of Eco RI-Sal I fragments containing Ava I multimers into the pSCW583

```
                          Schematic 1
                           pSCW627

Figure 3:
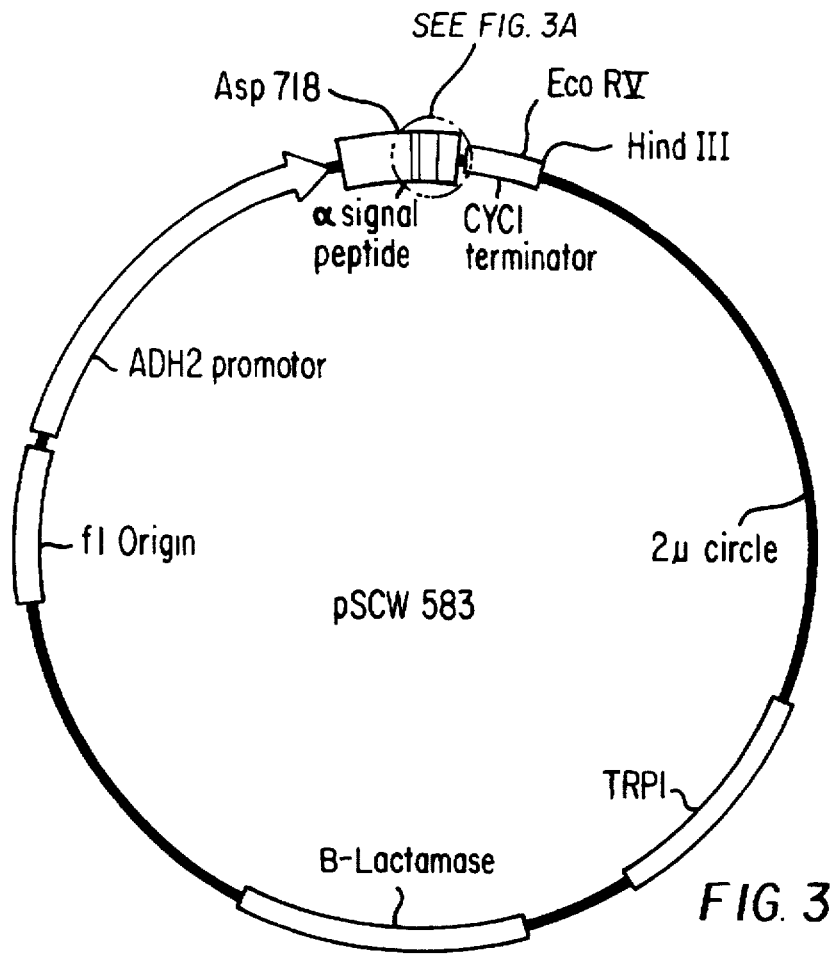
FIGS. 3 and 3A are schematic diagrams of the baker's yeast expression plasmid used in the recombinant preparation of one embodiment of the present invention, as described in Example 1 below.
Figure 3A:
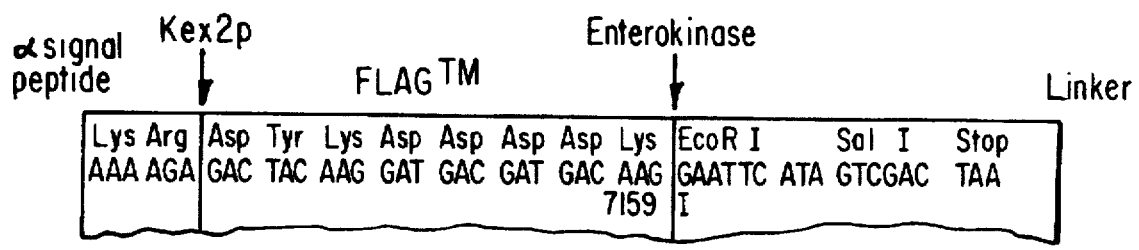

>Eco R I  >Ava I
     |         |
     |       10        20        30        40        50        60
     |        *         *         *         *         *         *
Top strand:    GAATTCGGTCCCGAGGGTCCACAAGGTCCAGAAGGTCCAGAAGGTCCAGAAGGTCCAGAA
Bottom strand: CTTAAGCCAGGGCTCCCAGGGTGTTCCAGGTCTTCCAGGTCTTCCAGGTCTTCCAGGTCTT >Ava I      >Sal I
                                              |           |
            70        80        90        100      Stop110
             *         *         *         *         |        *
          GGTCCACAAGGTCCAGAAGGTCCAGAAGGTCCAGAAGGTCCCGAGCTAAGTCGAC
          CCAGGTGTTCCAGGTCTTCCAGGTCTTCCAGGTCTTCCAGGGCTCGATTCAGCTG
                                                      |
``` extra base to align this stop codon to the reading frame of the alpha Lac Z start codon in the landing vector derived from pTZ18R Genescribe so that there is a good blue to white screen for the presence of cloned inserts A sample (1 mg) of pSCW1109 DNA was prepared by the method of Lee et al from a culture grown in the noted medium including ampicillin (150 µg/ml). The Ava I monomer nucleic acid encoding the GG monomer was prepared by restricting the pSCW1109 DNA with 2 Units of Ava I per µ DNA at 37° C. for 8 hours. A complete digest was obtained vector (FIG. 3), and not that in the lacZ reading frame of pSCW1143 (FIG. 1B). This illustrates the distinction of biopolymer DNA construction in *E. coli* from biopolymer secreted expression in *S. cerevisiae*. This Ava I site CCC GAG sequence, at which repeated GG monomer is inserted, is preceded first by a glycine codon to produce a starting GPE tripeptide in the GG biopolymer and secondly by a lysine codon acid for cleavage by the Trypsin protease. The Ava I site that precedes the stop codon and thus the biopolymer, as constructed, ends in a Gly-Pro-Glu tripeptide.

to the Kex2p cleavage site followed by the extra glycine codon and the appropriate Ava I site for landing GG multimers, was engineered. Biopolymer GG repeats were "landed" in this Ava I site, isolated and recloned into pSCW583 as Asp 718-Sal I DNA fragments. The result was

```
                    Schematic 2
                    pSCW1143 extra glycine codon, GGT, so that the yeast produced biopolymer will start
    with a glycine proline glutamic acid tripeptide since the Ava I encodes a
    proline glutamic acid dipeptide  |
                                     |
       Trypsin cleavage site         |
                       |    |
            Glu Phe Gly Lys Gly Pro Glu Stop
Top strand:  GAA TTC GGT AAG GGT CCC GAG TAA GTC GAC AAG CTT
Bottom strand:CTT AAG CCA TTC CCA GGG CTC ATT CAG CTG TTC GAA
    |           |   *        |   *       |   *        |
    |          10            |  20       |  30        |
    >                        >           >            >
    Eco R I                 Ava I       Sal I        Hind III
              10             20          30
```

To produce the GG biopolymer without any extraneous amino acids, the landing plasmid pSCW1253 was used. The pSCW1253 plasmid encodes the C-terminus of the yeast alpha factor secretory leader peptide, from the Asp 718 site to the encoded Lys Arg Kex2p protease site. The Kex2p protease cleaves the alpha secretion factor on the C-terminus side of the Lys Arg pair. Schematic 3 below (pSCW1253) also shows the reading frame that results from cloning of Asp 718-Sal I fragment containing Ava I multimer fragments into pSCW583 (FIG. 3), and not that in the lacZ reading frame of pSCW1253 (FIG. 1C). This again illustrates the distinction of biopolymer DNA construction in *E. coli* from biopolymer secreted expression in *S. cerevisiae*. The Ava I site, CCC GAC sequence, at which repeated GG monomer is inserted, follows first a glycine codon to produce a starting Gly-Pro-Glu tripeptide in the GG biopolymer and secondly a lys-arg codon pair as a Kex2p protease cleavage site. Additionally, a glutamic acid codon precedes the stop codons as part of the Ava I site, such that the biopolymer ends in a Gly-Pro-Glu tripeptide.

GG multimer DNA that encodes and produces SEQ ID NO:22 GG biopolymers upon secretion from yeast.

Each GG multimer pool ligation, whether landed in the Ava I of pSCW1143 or pSCW1253, was transformed into *E. coli* strain JM109 as previously described. The presence of clones containing inserts in pSCW1143 were analyzed for multimer size by Eco RI-Sal I double digests compared to molecular weight standards whereas clones containing inserts in pSCW1253 were analyzed for multimer size by Asp 718-Sal I double digests. Multimer insert containing clones were checked by Ava I solo digests for verification of correct multimer assembly and absence of recombination artifacts. Typically, greater than 80% of the colonies on the transformation plate contained clonal multimers. These clones were all observed to be uniformly stable with the complete absence of recombination artifacts. Additionally, all GG monomer or multimer clones (in pSCW1143 and pSCW1253 backbones) were a brilliant sapphire blue color which was more intense than the blue of the non-insert containing plasmids (pSCW1143 and pSCW1253) in JM109 on LB X-Gal transformation plates.

```
                        Schematic 3
                        pSCW1253 extra glycine codon, GGT, so that the yeast produced biopolymer will start
    with a glycine proline glutamic tripeptide since the Ava I encodes a
    proline glutamic acid dipeptide          |
                                             |
           Kex2p protease cleavage site      |       tandem Stop codons
                                |    |                      |
          ........... Val Pro Asp Lys Arg Gly Pro Glu StopStop
    GAA TTC CGG GTA CCA GAT AAG AGA GGT CCC GAG TAA TAA GTC GAC AAG CTT
    CTT AAG GCC CAT GGT CTA TTC TCT CCA GGG CTC ATT ATT CAG CTG TTC GAA
    |       | *          *           | *              *          | *
    |       | 10         20          | 30             40         | 50
    |       |                        |                |          |
    >       >                        >                >          >
    Eco R I Asp718                  Ava I           Sal I      Hind III
```

Figure 4A:
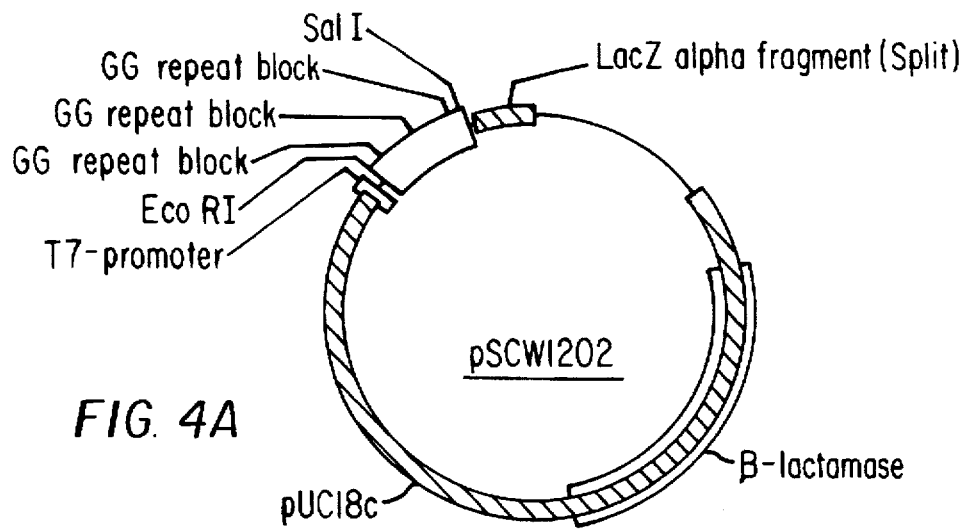
FIGS. 4A, 4B and 4C are schematic diagrams of the multimer plasmids used in the recombinant preparation of one embodiment of the present invention, as described in Example 1 below.
Figure 4B:
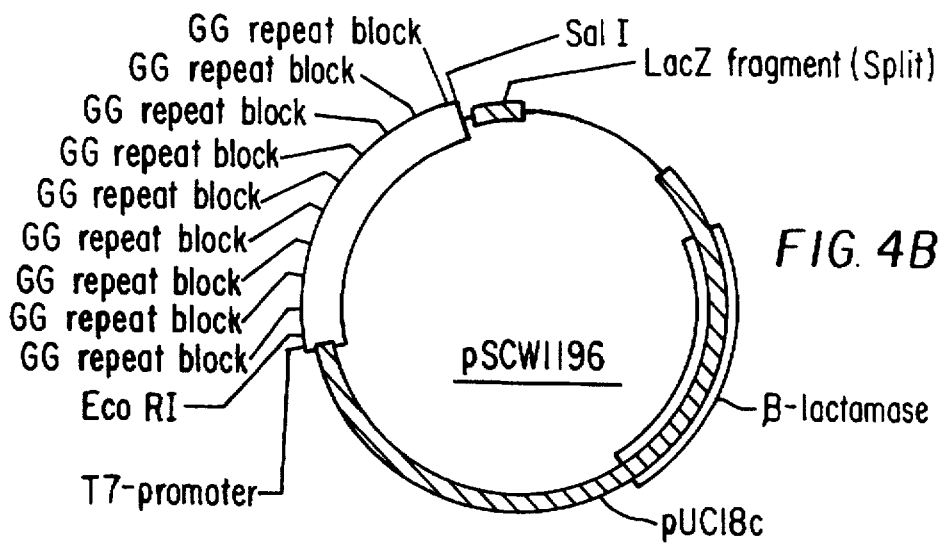
Figure 4C:
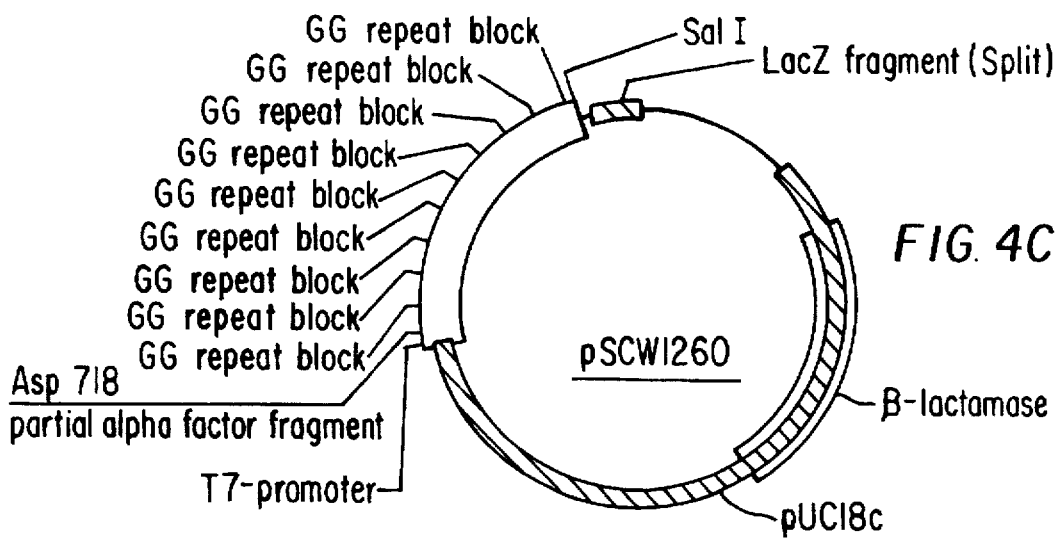

An Asp 718 site occurs in the yeast alpha factor signal secretion DNA sequence. The cleavage site for the yeast alpha signal protease, Kex2p (KEX2 gene product), is encoded in the yeast alpha factor signal DNA following this Asp 718 site. Therefore, a linker with an Asp 718 Sal I DNA fragment which encodes the amino acids normally found in the alpha factor secretion signal peptide from the Asp 718 up Two transformants in pSCW1143 backbones found to have the GG monomer DNA assembled into multimers of 3 and 9 were designated pSCW1202 and pSCW1196, respectively (FIGS. 4A and 4B). One transformant in a pSCW1253 backbone found to have the GG monomer DNA assembled into a multimer of 9 was designated pSCW1260 (FIG. 4C).

The baker's yeast protein expression vector pSCW583 contained DNA encoding the yeast alcohol dehydrogenase II promoter for regulated high transcriptional mRNA expression, the alpha factor pre-pro-region for translational initiation and extracellular secretion, the Kex2p cleavage site to remove the alpha factor pre-pro-region from -the biopolymer, the FLAG™ epitope, a short Eco RI-Sal I polylinker to clone the assembled biopolymer, a CYC1 bidirectional transcriptional mRNA terminator, the yeast TRP1 gene for selection in yeast, yeast 2 micron circle elements for high copy plasmid control in yeast, the E. coli bla gene for antibiotic selection in E. coli, and pBR322 elements for high copy control in E. coli.

Multimers pSCW1202 (3 repeats of the GG monomer) and pSCW1196 (9 repeats of the GG monomer) were used as the source of a Eco RI-Sal I DNA polymer block containing the repeated GG monomer DNA for ligation at the same sites into the S. cerevisiae protein expression vector, PSCW583. Ligation of these DNA fragments was by the previously described standard method. The ligation reactions were transformed into E. coli strain JM109 and the transformants selected for ampicillin resistance by the previously described standard methods.

pSCW1260 (9 repeats of the GG monomer) was used as the source of Asp 718-Sal I DNA polymer block containing the repeated GG monomer DNA for ligation at the same sites into the S. cerevisiae protein expression vector, pSCW583. Ligation of these DNA fragments was carried out by the previously described standard method. The ligation reactions were transformed into E. coli strain JM109 and the transformants selected for ampicillin resistance by the standard methods previously described.

Figure 5A:
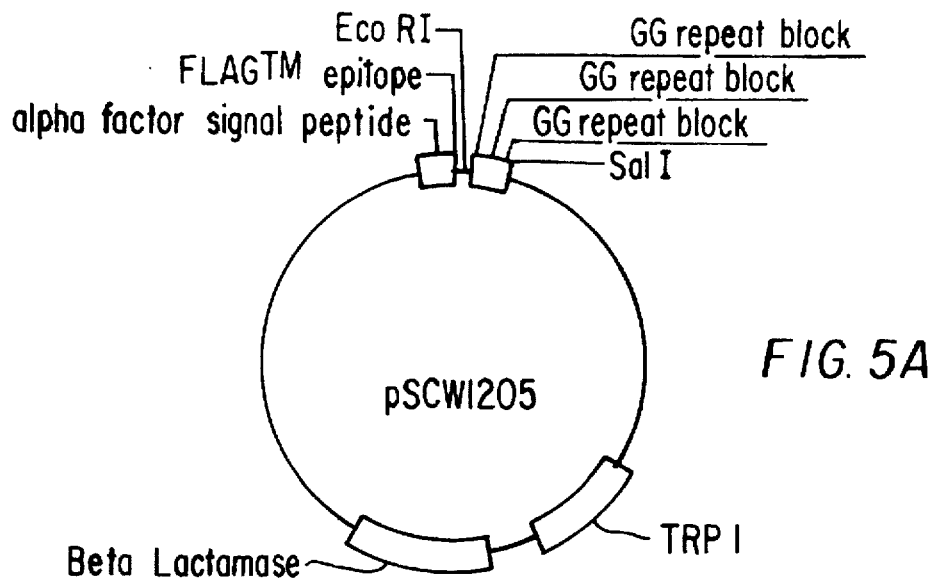
FIGS. 5A, 5B and 5C are schematic diagrams of the biopolymer yeast expression plasmids constructed and used in Example 1 below.
Figure 5B:
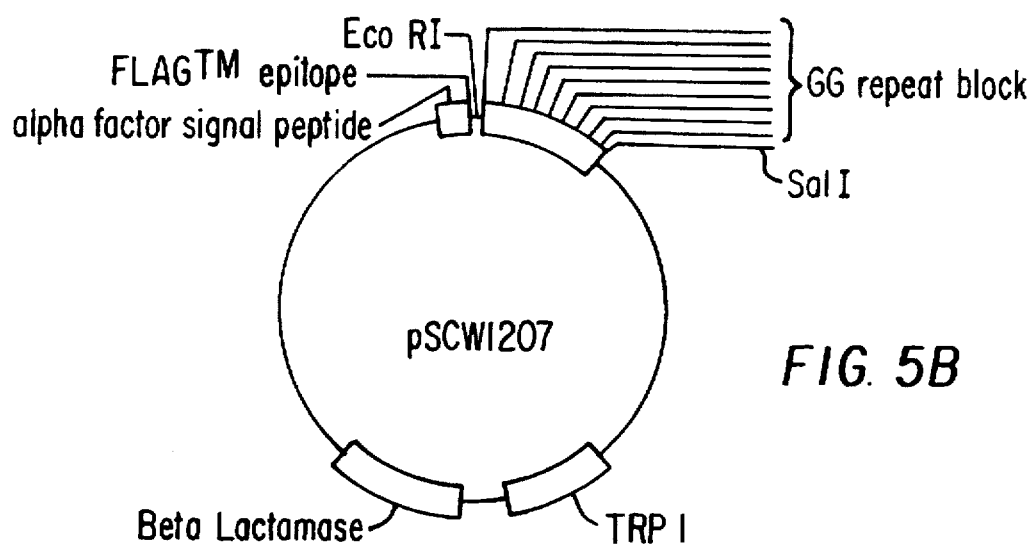

Transformants derived from the ligations of pSCW1202 and pSCW1196 multimer DNA (destined to be FLAG™lysine epitope biopolymers) into the pSCW583 yeast expression vector were screened by Eco RI-Sal I double digests to confirm correct multimer size and by Ava I solo digests to confirm genetic stability. Two transformants were designated GG biopolymer yeast expression plasmids, pSCW1205 and pSCW1207 (FIGS. 5A and 5B). In yeast, pSCW1205 produces FLAG™epitope Trypsin site N-terminally tagged 3 repeat GG biopolymer having the sequence:

SEQ ID NO: 19:
Asp Tyr Lys (Asp)₄ Lys Glu Phe Gly Lys* Gly Pro Glu {[(Gly Pro Gln)(Gly Pro Glu)₄]₂}₃, while pSCW1207 produces the sequence:

SEQ ID NO: 20:
Asp Tyr Lys (Asp)₄ Lys Glu Phe Gly Lys* Gly Pro Glu {[(Gly Pro Gln)(Gly Pro Glu)₄]₂}₉.

In this example, after production and purification, the extra N-terminus amino acids of the biopolymer were removed by Trypsin digestion at the lysine*. The bipolymer was re-purified and processed to the form of SEQ ID NO:3.

Figure 5C:
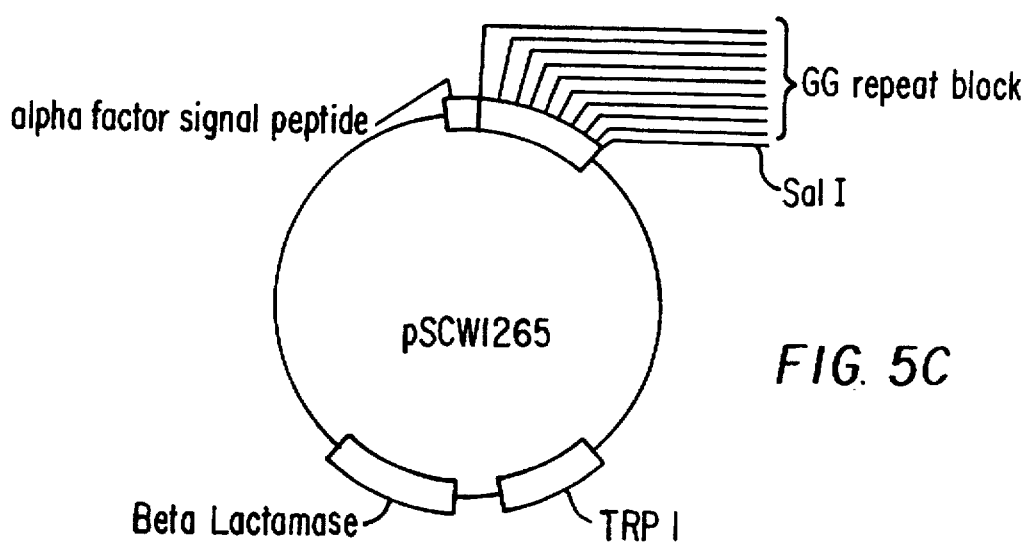

Transformants derived from the ligation of pSCW1260 multimer DNA (destined to be SEQ ID NO:3) into the yeast expression vector pSCW583 were screened by Asp718-Sal I double digests to confirm correct multimer size and by Ava I solo digests to confirm genetic stability. One transformant was designated pSCW1265 (FIG. 5C), which produces SEQ ID NO:3 in yeast. pSCW1205 (SEQ ID NO:19), pSCW1207 (SEQ ID NO:20) and pSCW1265 (SEQ ID NO:3) were transformed by standard electroporation with a conventional Bethesda Research Electroporator into S. cerevisiae strain BJ3505 (available from the Yeast Genetic Stock Center, University of California, Berkeley). This strain has the genotype (mating type a pep4::HIS3 prb1-1. 6R HIS3 lys2-208 trp1-101 ura3-52 gal2 can1). The protease deficient properties of this strain are well known. The pep4::HIS3 mutation inactivates the structural gene, PEP4, which encodes the PrA protease (an aspartic class endoprotease) whereas the prb1-1. 6R mutation inactivates the structural gene, PRB1, which encodes the PrB protease (a serine class subtilisin-like endoprotease). Both PrA and PrB are lumenal vacuoler proteases. PrB in particular is expressed at high levels in stationary culture conditions.

Transformants were selected for TRP1 complementation on Synthetic Complete media (minus tryptophan) plates by standard methods (Methods in Yeast Genetics, Laboratory Manual, Cold Spring Harbor Press, 1981 and Guide to Yeast Genetics and Molecular Biology, Methods in Enzymology, Vol. 194, Academic Press, Inc., 1991).

BJ3505 transformants of pSCW1205, pSCW1207 and pSCW1265 were first grown for 48 hours on a roller at 30° C. to early stationary phase in 5 ml of liquid Synthetic Complete (minus tryptophan) media. These cultures were then rediluted to 1% v/v in 50 ml of the same media and grown on a rotary shaker at 175 revolutions per minute to early stationary phase (about 8 OD units at 600 nm) at 30° C. Finally, the culture were diluted to 4% by volume into one liter of production media and grown for 70 hours on a rotary shaker at 175 revolutions per minute at 30° C. in a 2.8 liter baffled fernbach flask. Several different production media may be used with or without the addition of calcium as a counter ion for the biopolymer and/or the yeast cell wall. YP1 production media contained 10% w/v yeast extract, 20% w/v Bactopeptone, 1% w/v dextrose and 3% w/v glycerol. YP4 production media contained 10% w/v yeast extract, 80% w/v Bactopeptone, 1% w/v dextrose and 3% w/v glycerol. Either a YP1 or YP4 optimized media supplemented with calcium chloride (20 millimolar) can be used for high production of GG biopolymers. YP1 production media supplemented with 20 mmolar calcium chloride provided a preferable compromise of high expression (about 500 mg/l) and low background of media protein impurities.

A pseudo plasticity in the GG biopolymer production culture was observed in some cases at 24 hours of culture growth when carefully examined and compared to a negative control culture. This pseudo plasticity Theologically shear thins when the culture was stirred with a rod. The pseudo plasticity occurs in a time dependent culture growth state only upon high level secreted expression of the SEQ ID NOS:1, 2, 3, 19 and 20 biopolymers (with or without the FLAG™N-terminus epitope) and not for other secreted proteins. This phenomenon was observed much more easily in partially or purified GG biopolymer fractions. It is biopolymer length, concentration, temperature and ionic strength dependent, and lowers the specific gravity of the production culture broth compared to a negative control culture.

The purification of SEQ ID NO:20 (pSCW1207 in S. cerevisiae strain BJ3505) and the removal of the FLAG™epitope to produce SEQ ID NO:3 is described below. Twenty liters of broth from BJ3505 transformed with pSCW1207 was prepared from twenty separate one liter fernbach cultures grown by the YP1 culture conditions described above. To remove the yeast cells and produce a culture supernatant (S1), the 20 liters of culture broth were centrifuged at 10,000 g for 10 minutes. The supernatant was sometimes filter sterilized using a 1,000,000 molecular weight cutoff conventional Filtron tangential flow filtration unit to produce a second supernatant (S2), that was devoid of yeast cells.

Twenty liters of either S1 or S2 were brought to pH 3.2 with hydrochloric acid to precipitate (overnight at 4° C.) the biopolymer preferentially over the other broth components. The acidified supernatants of S1 or S2 were centrifuged at 10,000 g for 20 minutes to produce a supernatant (S3) that was discarded, and a pellet (P3) containing the desired biopolymer. The P3 pellet was then resuspended in 2 liters (one tenth the original culture volume) of tris (hydroxymethyl)amino methane buffer (50 mmolar, pH 7.8) containing sodium chloride (200 mmolar), ethylenediaminetetraacetic acid (20 mmolar) and phenylmethylsulfonyl fluoride (1 mmolar) and clarified by centrifugation at 10,000 g for 20 minutes. The desired biopolymer (SEQ ID NO:20) was in the supernatant (S4), and the residual pellet (P4) was discarded.

The biopolymer was purified by ion exchange chromatography. The S4 supernatant was applied to a commercial 10 cm×30 cm (4 liter) DEAE Sephacel ion exchange column. -The column was washed with 80 liters (20 column volumes) of tris(hydroxymethyl)aminomethane buffer (50 mmolar, pH 7.8) containing sodium chloride (200 mmolar) at a flow rate of 3 liters per hour and a pressure of 0.3 atmospheres until the eluant had an absorbance less than 0.001 OD at 214 nm. The FLAG™GG 9-mer (SEQ ID NO:20) was eluted at a flow rate of 3 liters/hour with a step gradient of buffer (50 mmolar, pH 7.8) containing sodium chloride (375 mmolar) in 500 ml fractions into 4 liters. The fractions containing the biopolymer, as determined by conventional SDS acrylamide electrophoresis, were pooled and designated fraction F1.

The FLAG™N-terminal epitope was removed by Trypsin proteolytic cleavage at the C-terminal side of the lysine* immediately proceeding the first repeating tripeptide (GPE) in the biopolymer to produce a cleaved unwanted peptide and the desired SEQ ID NO:3. To cleave the epitope, a sample (1 g) of fraction F1 was reacted with 400 units Trypsin (type XI DPCC treated) per mg of biopolymer per ml of calcium chloride (20 inmolar) in buffer (100 mmolar, pH 8.5) at 37° C. for 18 hours. The reaction was completely dependent upon the presence of calcium chloride. The completeness of the reaction was determined to be essentially 100% by estimating the relative mobility on SDS gels of the Trypsin treated sample relative to the mobility of the starting fraction F1. The Trypsin cleaved biopolymer migrated faster on SDS acrylamide electrophoresis than the uncleaved biopolymer with a relative Rf of 1.10. The Trypsin cleaved biopolymer reaction solution was designated fraction F2. The use of Trypsin additionally provides a means to remove potential trace amounts-of protein that are not detectable by standard analytical means such as absorbance at 280 nm, Coomassie Blue R-250 staining of SDS electrophoresis gels, GHOST Bands™Protein Detection System (Promega Corporation) or silver staining of SDS electrophoresis gels.

The apparent molecular weights determined from the SDS gel migration distances relative to the molecular weight markers for the uncleaved and the cleaved biopolymers were 40 kd and 38 kd, respectively. The calculated molecular weights from the primary amino acid sequence are 27,177 daltons and 25,778 daltons, respectively. It is known for collagen and gelatin fragments that their apparent molecular weight is about 1.4 times larger than their true primary sequence molecular weight ("Estimation of the Size of Collagenous Proteins by Electrophoresis and Gel Chromatography", *Methods in Enzymolocry*, 1982, Vol. 82, Section 19, pp. 410–423). The ratio of the apparent molecular weight to the primary sequence molecular weight for the uncleaved and cleaved biopolymers was about 1.47 and is thus consistent with the known anomalous molecular weight behavior of collagen and gelatin fragments.

SEQ ID NO:3 stained pink with Coomassie Blue R-250 in a transitory manner only during the early phase of destaining in 10% acetic acid and 5% methanol and at the end point of destaining was not visible at all. The FLAG™epitope on the biopolymer (SEQ ID NO:20) serves to enable detection by Coomassie Blue R-250 staining. However, the FLAG™epitope did not. enable detection by M1 or M2 monoclonal antibodies on Western blots of SDS gels. Therefore to detect the processed biopolymer without the FLAG™epitope, SDS gels were visualized using a commercially available negative stain utilizing copper containing solutions (GHOST BANDS™Protein Detection System).

Alternatively, to reproducibly and conveniently detect the FLAG™-containing biopolymer, the cationic carbocyanine dye, 4,5,4', 5'-dibenzo-3,3'-diethyl-9-methyl-thiacarbocyanine bromide (also known as "Stains-All") was used. The noted biopolymer stained a chrome blue-green color against a pink background.

SEQ ID NO:3 from fraction F2 was purified on a FRACTOGEL™tentacle polymer ion exchange matrix (from EM Separations, Division of EM Industries, Inc.). One gram of Trypsin cleaved biopolymer in 1 liter of fraction F2 reaction buffer mix was brought to a final ethylenediaminetetraacetic acid concentration (40 mmolar) and applied to a 5×30 cm (0.5 liter) DMAE FRACTOGEL™tentacle polymer ion exchange column in tris(hydroxymethyl)aminomethane (50 mmolar, pH 8.0) containing sodium chloride (50 mmolar) at a cross sectional flow rate of 45 ml/hour/cm$^2$. The addition of ethylenediaminetetraacetic acid (40 mmolar) complexed the calcium chloride (20 mmolar) from the fraction F2 reaction buffer mix. The calcium chloride was observed to cause elution of the SEQ ID NO:3 biopolymer at variable sodium chloride concentrations from the FRACTOGEL™tentacle polymer ion exchange matrix. The cleaved FLAG™peptide and Trypsin self-digestion peptide fragments were eluted with 4 column volumes of tris(hydroxymethyl)aminomethane buffer (50 mmolar, pH 8.0) containing sodium chloride (300 mmolar), as assayed by a very low ratio Of $A_{214}/A_{280}$ of less than 5.

Residual uncleaved biopolymer was eluted with 2 column volumes in half column volume steps of buffer (50 mmolar, pH 8.0) containing sodium chloride (400 mmolar) as assayed by a low ratio of $A_{214}/A_{280}$ of 41. SEQ ID NO:3 was eluted in a pure form with 2 column volumes in half column volume, steps of buffer (50 mmolar, pH 8.0) containing sodium chloride (600 mmolar) as assayed by a very high ratio of $A_{214}/A_{280}$ Of 281. The fractions containing the pure biopolymer were pooled and designated fraction F3.

In order to prepare and purify the biopolymer in a form suitable for use in photographic silver halide emulsions, including the controlled formation of silver halide crystals containing tabular or other morphologies, the biopolymer was dialyzed until the residual ions were potassium cations and nitrate anions. At the concentrations Involved, these ions do not change the photographic properties of silver halides, whereas the original buffer, a primary amine, may affect them. A sample (750 mg) of pure SEQ ID NO:3 biopolymer fraction F3 (at a concentration of 1 mg/ml) was brought to a final concentration of ethylenediaminetetraacetic acid (20 mmolar) and dialyzed in SPECTRAPOR Seven 3,500 molecular weight, low metal and low sulfur containing dialysis tubing three times with 20 liters of deionized water (18 Megaohms/cm), 2 times with 1 mmolar potassium nitrate and two times with deionized water (18 Megaohms/cm). The dialyzed pure biopolymer was freeze dried into a fluffy white powder and designated as fraction F4.

To prepare the dialyzed pure biopolymer in a form suitable for silver halide application, it was desalted by gel chromatography to remove excess potassium and nitrate counter ions. The dialyzed fraction F4 (750 mg) was dissolved (about 0.75% w/v) into 98 ml of 0.22 µm filtered deionized water, warmed to 45° C. and held at that temperature for 30 minutes. It was then applied at a cross sectional flow rate of 45 ml/hour/cm² onto a 5 cm×18 cm (0.5 liter) G-25 Sephadex column in 0.22 µm filtered deionized water. The column was eluted in 0.22 µm filtered deionized water (18 Megaohms/cm) in a drop-wise manner into 8 ml constant drop fractions. The use of 0.22 µm filtered deionized water (18 Megaohms/cm) eliminates the possibility of particulate contaminants that might affect nucleation, growth or photographic sensitivity of silver halide grains, including tabular silver halide grains. The G-25 desalted biopolymer eluted as expected for classical desalting chromatography at the excluded volume and with some tailing past the void volume. Strikingly, the constant drop fractions containing the G-25 desalted pure biopolymer had almost a 15% increase in volume (about 9.2 ml) compared to fractions containing water or residual desalted ions (8 ml). Constant drop fractions were pooled beginning at the excluded volume which contained pure SEQ ID NO:3 (as determined by a high ratio of $A_{214}/A_{280}$ of 281) until the fractions began to show an increase in conductivity due to the emergence of ion impurities at the void volume (as determined by conductivity). The yield was determined by the use of a molar absorption constant at 214 nm of 241,000, based on the molar absorption constant at 214 nm of the GG monomer, 26,777, scaled to the molecular weight of the GG biopolymer. Later, this molar absorption constant was determined directly on the biopolymer and found to be accurate. A total of 675 mg of desalted pure biopolymer was recovered. The liquid desalted pure biopolymer was designated fraction F5.

To deliver the liquid desalted pure biopolymer in a convenient form for photographic emulsion precipitation, fraction F5 was freeze dried. Upon freeze drying, it became a clear transparent film that did not shatter but could be torn with the release of fibrils along the torn edges. The freeze dried desalted pure biopolymer was designated fraction F6.

The freeze dried desalted pure biopolymer was characterized at the Analytical and Synthetic Facility, Cornell Biotechnology Center, for amino acid composition by standard means of acid hydrolysis, ion chromatography and fluorescent detection. The following analysis was determined:

| Amino Acid | pMolar |
|---|---|
| Asx | 88.3 |
| Glx | 4830 |
| Ser | 11.4 |
| Gly | 4820 |
| His | <5 |
| Arg | 6.8 |
| Thr | 14.2 |
| Ala | 16.2 |
| Pro | 4850 |
| Tyr | 18.8 |
| Val | 6.8 |
| Met | 9.7 |
| Cys | <10 |
| Ile | <5 |

-continued

| Amino Acid | pMolar |
|---|---|
| Leu | 6.5 |
| Phe | 25.2 |
| Lys | 51.7 |

SEQ ID NO:3 was found to have an amino acid composition of glycine, proline and glutamic acid in a 1:1:1 molar ratio. This composition is consistent with the predicted amino acid composition since glutamines deamidate during the acid hydrolysis sample preparation. To crudely estimate the purity of the biopolymer in this sample, one can add the amounts of all amino acids present that are not contained by the biopolymer and divide by the amount of amino acids contained by the biopolymer. The result is a purity of at least 98.6%.

The freeze dried desalted pure biopolymer was also characterized by the Analytical and Synthetic Facility, Cornell Biotechnology Center for the N-terminus amino acid sequence. It was found to have an amino acid sequence as predicted beginning after the lysine for Trypsin cleavage through the next 40 amino acids. The three glutamines in the first 40 amino acids were found to be fully amidated. It is likely that the remaining encoded glutamines in the biopolymer are amidated glutamines as well.

The FLAG™ containing biopolymer (SEQ ID NO:20) was also characterized by N-terminus amino acid sequencing. It was found to have an amino acid sequence beginning with the FLAG™ epitope and then through the first 40 amino acids of the biopolymer. This demonstrates that upon secretion of this biopolymer the Kex2p protease correctly cleaved at the C-terminal side of the encoded Lys-Arg cleavage site to correctly expose a free N-terminal FLAG™ epitope. The inability to detect the biopolymer by the M1 or M2 FLAG™ anti-antibody on Western blots as previously described is therefore for some other reason than the mere absence of the target epitope.

The freeze dried desalted pure biopolymer was also characterized at the Analytical and Synthetic Facility for molecular weight by laser desorption mass spectrometry on a commercially available FinniganMat instrument. It was found to have a molecular weight of 26,001 daltons. This agrees well (within experimental error) with the predicted 25,778 daltons. The difference in molecular weights may be because of 4 or 5 residual strongly bound calcium ions.

EXAMPLE 2

Synthetic Preparation of Biopolymer

A biopolymer of the present invention was prepared by chemical synthesis of the polypeptides (SEQ ID NO:4 and 6–14) in the following manner.

Each of the noted polypeptides was synthesized by continuous flow solid phase techniques on a commercially available Milligen Corporation Model 9050 Peptide Synthesizer using the 9-fluorenylmethoxycarbonyl (Fmoc) amino terminal protection strategy known in the art (see, for example, Atherton et al, *Solid Phase Peptide Synthesis*, IRL Press, New York, N.Y. 1989, and Bodansky, *Principles of Peptide Synthesis*, Springer-Verlag, New York, N.Y., 1984). The solid phase peptide synthesis protocol consisted of N-1 cycles where N is the number of amino acids in the desired polypeptide. Each cycle consisted of four steps: "deblocking", "activating", "coupling" and "capping". After the final cycle, the protocol included a "cleavage/deprotection" step.

The solid phase support used in these procedures was a polyamide-kieselguhr composite having a covalently attached 4-hydroxymethylphenoxyacetic acid linking group (available as Pepsyn-KA from Milligen Corporation). This material was provided with the Fmoc protected carboxy terminal amino acid already attached. In all cases, 2.7 grams of this support material were used, slurried in a minimum volume of amine free N,N-dimethylformamide, and packed in a synthesis column (1×10 cm). A gap (0.5 cm) was left at the top of the column to allow for the expansion of the support material due to the growth of the peptide chain during synthesis. In general, the loading of the solid phase support was 0.09 milliequivalents/g of support. This was confirmed by removing the Fmoc group quantitatively from a weighted quantity of support in a known volume of 20% (v/v) piperidine in N,N-dimethylformamide. The amount of loaded amino acid was determined from the concentration of the Fmoc-piperidine adduct by measuring the absorbance of the solution at 301 nm $\epsilon_{301}$ =7,800 molar$^{-1}$cm$^{-1}$.

"Deblocking Step":

The Fmoc groups were removed using a seven minute column wash of a 20% piperidine/N,N-dimethyl formamide mixture. The extent of Fmoc removal was determined by monitoring the column effluent at 313 nm by means of an on line UV detection. When all of the Fmoc had been removed, the column was washed with amine-free N,N-dimethylformamide for 12 minutes.

"Activating/Coupling Steps":

After all of the 20% piperidine was removed from the column, an acylation step (addition of the next Fmoc amino acid) was begun. The coupling strategy employed was 1-hydroxybenzotriazole mediated active ester acylation. In this approach, an excess (3.4 equivalents) of the Fmoc protected active esters was dissolved immediately before use in a small volume (2.5 ml) of 5% solution of 1-hydroxybenzotriazole in N,N-dimethylformamide.

The active ester-Hobt acylation solution was injected into the column and recirculated by means of a pump at a flow rate of about 5.0 ml/minute. The progress of the acylation was monitored by an on line UV detector at 313 nm. The standard acylation time was 30 minutes. However, this was increased when necessary to as much as 120 minutes. After coupling was complete, the acylation solution was washed from the column with an extensive N,N-dimethylformamide wash.

Two types of Fmoc protected preformed active esters of the amino acids were obtained from Milligen Corporation. For most amino acids (all except threonine and serine), pentafluorophenyl esters were employed. However, for threonine and serine, 3-hydroxy-1,2-dihydro-4-oxo-benzotriazine esters were used. The quality of the active esters was confirmed by thin layer chromatography on activated silica plates in a mixture of chloroform, methanol and acetonitrile (90:5:5 v/v ratio). The side chain protecting strategy varied with the amino acid. For example, for alanine, asparagine, glycine, isoleucine, leucine, methionine, phenylalanine, proline, tryptophan, valine and glutamine, no protection was needed. For arginine, 4-methoxy-2,3,6-trimethylbenzenesulfonyl was used for protection, and for histidine and cysteine, triphenylmethyl was used for protection. For lysine, protection was afforded by Nα-t-butoxycarbonyl, and t-butyl was used for aspartic acid, glutamic acid, serine, threonine and tyrosine.

"Capping Step":

Any remaining unreacted alpha amino acid groups were then capped by washing the column for 12 minutes with a solution of acetic anhydride (0.5 molar) and pyridine (0.5 molar) in N,N-dimethylformamide. This was done to eliminate internal deletions, and to facilitate the purification of the desired product. The capping solution was removed by washing the system with N,N-dimethylformamide.

As noted above, these steps were repeated for each new amino acid added to the peptide chain. When the desired length and sequence of amino acids were reached, the synthesis was complete. The last Fmoc group was removed as described above, and the 20% piperidine solution was washed out first with N,N-dimethylformamide and then with dichloromethane.

"Cleavage/Deprotection Step":

The product polypeptide resign was removed from the column and dried under reduced pressure. The dried polypeptide was cleaved from the support, and the protective side chains removed by treatment with trifluoroacetic acid which contained a scavenger to avoid side reaction that might occur at some of the labile side chain functional groups. The polypeptide was suspended in a cleavage reagent mixture of trifluoroacetic acid, thioanisole, ethanedithiol and anisole (90:5:3:2 v/v ratio) with gentle agitation. After 2 hours, the solid support was separated from the soluble deprotected polypeptide by filtration. The solvent and scavengers were removed by roto-evaporation. The polypeptide product was precipitated with ether and chilled to 4° C., and the precipitate was spun down in a centrifuge and the ether decanted. The precipitate was then redissolved in 5% acetic acid, and extracted against 3 volumes of ether. The aqueous layer was then filtered and purified by reverse phase high pressure liquid chromatography.

The desired polypeptide product was identified by mass spectrometry and its purity was checked by two dimensions of high pressure liquid chromatography. If either of the dimensions indicated the presence of more than 5% impurities, the material was repurified. The purified material was then lyophilized and stored desiccated at −20° C.

EXAMPLE 3

Use of Biopolymers to Prepare Photographic Emulsions of Various Grain morphology This example describes the preparation of several silver halide emulsions using several different biopolymers of this invention as peptizers, and the types of grain morphologies obtained thereby. Each biopolymer in the first set of experiments was prepared using the procedure described above in Example 2.

The biopolymer peptizer (0.1 weight %) and an aqueous solution of sodium bromide (1.09 g/l) were added to a reaction vessel. The contents were maintained at 50° C. while silver nitrate (2 molar) was added over a period of 45 seconds, along with sufficient halide salts (2 molar, 99.5 mole % of sodium bromide and 0.5 mole % of potassium iodide) to maintain the initial halide concentration. After a 1 minute delay, additional salts were added to bring the concentration of sodium bromide to 2.69 g/l. The temperature was then raised to 60° C..

Oxidized gelatin was added to provide a concentration of 0.7 weight %. Silver nitrate (2 molar) was then added over a 40 minute period at an increasing rate, matched by sufficient salts to maintain the new halide concentration. Finally, silver nitrate was added alone, slowly, to reduce the bromide concentration by a factor of 6.

The resulting emulsions were evaluated by taking scanning electron micrographs, and the average grain morphology and dimensions were determined using conventional techniques.

The capacity (affinity) of the given biopolymer to bind silver ion was also measured at pH 6.9–7.0 as follows:

Silver nitrate ($5\times10^{-6}$ molar), potassium nitrate (0.1 molar) and the biopolymer (0.3 weight %) were mixed at 23° C. in pH 7.0 phosphate buffer solution. The "vAg" of this solution is the potential of a bare silver electrode against a Ag/AgCl reference electrode in a salt bridge assembly. For comparison purposes, the "vAg" of a similar solution without the biopolymer was measured, and the difference in vAg readings is identified as Δ vAg for the biopolymer.

Table I below lists the bipolymers used as peptizers, the resulting "major" (predominant) grain morphologies, average grain sizes, and the biopolymer binding affinities for silver ion. It is apparent that the biopolymers which bind silver ion strongly (greater than 50 Δ vAg) provide non-tabular grain morphologies, such as octahedral morphology. Weaker binding biopolymers (less than 50 Δ vAg binding affinity) provide grains with thin tabular morphology.

TABLE I

| Biopolymer Peptizer | Major Morphology | Average Size (μm) | Δ vAg |
|---|---|---|---|
| SEQ ID No: 11 | Octahedral (70%) | 0.6 | 102 |
| SEQ ID No: 12 | Irregular (60%) | 0.4 | 117 |
| SEQ ID No: 13 | Octahedral (90%) | 0.6 | 58 |
| SEQ ID No: 6 | Tabular (80%) | *1.3 × 0.055 | 28 |
| SEQ ID No: 7 | Tabular (50%) | *1.9 × 0.065 | 7 |
| SEQ ID No: 8 | Tabular (85%) | *1.3 × 0.052 | 2 |
| SEQ ID No: 9 | Tabular (85%) | *1.3 × 0.047 | 12 |

TABLE I-continued

| Biopolymer Peptizer | Major Morphology | Average Size (μm) | Δ vAg |
|---|---|---|---|
| SEQ ID No: 10 | Tabular (88%) | *1.3 × 0.047 | 2 |

*The two dimensions refer to equivalent circular diameter and grain thickness, respectively.

In a second experiment, the biopolymer identified herein as SEQ ID NO:3 was prepared using the recombinant DNA preparatory procedure described in the Example 1 above. It was used as a nucleation peptizer to prepare an emulsion using the procedure described above except that the biopolymer was also used as peptizer in the growth segment of emulsion preparation in place of oxidized gelatin.

The resulting emulsion was evaluated using a scanning electron microscope (as described above), and found to have predominantly grains having a thin tabular morphology. This demonstrates the usefulness of biopolymers prepared using recombinant DNA technology to make uniform thin tabular silver halide emulsions. The emulsion grains in this emulsion had an average thickness of 0.074 μm and an average equivalent circular diameter of 0.55 μm.

The invention has been described in detail with particular reference to preferred embodiments thereof, but it will be understood that variations and modifications can be effected within the spirit and scope of the invention.

We claim:

1. A recombinant nucleic acid comprising a nucleotide sequence which encodes a peptide sequence represented by the formula:

I:
{[(Gly Pro Gln)(Gly Pro Glu)$_4$]$_2$}$_n$,
SEQ ID NO: 4

II:
Gly Pro Glu{[(Gly Pro Gln)(Gly Pro Glu)$_4$]$_2$}$_n$,
SEQ ID NO: 1 or

III:
Gly Pro Xaa$_1$ Gly Leu Xaa$_2$ Gly Pro Arg Gly Pro Pro
Gly Ala Ser Gly Ala Pro Gly Pro Glu Gly Phe Gln Gly,
SEQ ID NO: 6 wherein Xaa$_1$ and Xaa$_2$ are independently the amino acids identified as Met, Ile, His, Lys, Asn, Tyr or Gly, and n is 1 to 25, or its nucleotide complement.

2. A recombinant nucleic acid comprising a nucleotide sequence which encodes a recombinant biopolymer having at least one occurrence of an amino acid sequence represented by the formula;

I:
{[(Gly Pro Gln)(Gly Pro Glu)$_4$]$_2$}$_n$,
SEQ ID NO: 4

II:
Gly Pro Glu{[(Gly Pro Gln)(Gly Pro Glu)$_4$]$_2$}$_n$,
SEQ ID NO: 1 or

III:
Gly Pro Xaa$_1$ Gly Leu Xaa$_2$ Gly Pro Arg Gly Pro Pro
Gly Ala Ser Gly Ala Pro Gly Pro Glu Gly Phe Gln Gly,
SEQ ID NO: 6 wherein Xaa$_1$, and Xaa2 are independently the amino acids identified as Met, Ile, His, Lys, Asn, Tyr or Gly, and n is 1 to 25, or its nucleotide complement.

3. A vector comprising a nucleic acid comprising a nucleotide sequence which encodes a recombinant biopolymer having at least one occurrence of a sequence represented by the formula:

I:
{[(Gly Pro Gln)(Gly Pro Glu)$_4$]$_2$}$_n$,
SEQ ID NO: 4

II:
Gly Pro Glu{[(Gly Pro Gln)(Gly Pro Glu)$_4$]$_2$}$_n$,
SEQ ID NO: 1 or

III:
Gly Pro Xaa$_1$ Gly Leu Xaa$_2$ Gly Pro Arg Gly Pro Pro
Gly Ala Ser Gly Ala Pro Gly Pro Glu Gly Phe Gln Gly,
SEQ ID NO: 6 wherein Xaa$_1$ and Xaa$_2$ are independently the amino acids identified as Met, Ile, His, Lys, Asn, Tyr or Gly, and n is 1 to 25, or its nucleotide complement.

4. A host cell containing a recombinant vector comprising the nucleic acid of claim 1 wherein said nucleic acid is operationally linked to nucleic acid sequences which allow expression of said nucleic acid in said host cell.

5. A host cell containing a recombinant vector comprising the nucleic acid of claim 2 wherein said nucleic acid is operationally linked to nucleic acid sequences which allow expression of said nucleic acid in said host cell.

6. The nucleic acid of claim 1 wherein n is 3 to 20.

7. The nucleic acid of claim 1 wherein said peptide sequence is selected from the group consisting of SEQ ID NO: 1:
Gly Pro Glu{[(Gly Pro Gln)(Gly Pro Glu)$_4$]$_2$}$_3$
SEQ ID NO: 2:
Gly Pro Glu{[(Gly Pro Gln)(Gly Pro Glu)$_4$]$_2$}$_4$
SEQ ID NO: 3:
Gly Pro Glu{[(Gly Pro Gln)(Gly Pro Glu)$_4$]$_2$}$_9$.

8. The nucleic acid of claim 1 wherein Xaa$_1$, and Xaa$_2$ are the same amino acids.

9. The nucleic acid of claim 8 wherein Xaa$_1$ and Xaa$_2$ are each Ile, Lys, Asn, Tyr or Gln.

10. The nucleic acid of claim 9 wherein Xaa$_1$ and Xaa$_2$ are each Gln.

11. The nucleic acid of claim 1 wherein Xaa$_1$ and Xaa$_2$ are each Met or His.

12. The nucleic acid of claim 2 for encoding said biopolymer having said peptide sequence that is present throughout said biopolymer at least 3 times.

* * * * *